US011701459B2

(12) United States Patent
Updyke et al.

(10) Patent No.: US 11,701,459 B2
(45) Date of Patent: Jul. 18, 2023

(54) UNIVERSAL PORTABLE ARTIFICIAL KIDNEY FOR HEMODIALYSIS AND PERITONEAL DIALYSIS

(71) Applicant: Fresenius Medical Care Holdings, Inc., Waltham, MA (US)

(72) Inventors: Palmer David Updyke, Walnut Creek, CA (US); Barry Fulkerson, Longmont, CO (US); Amaury De Leon De Leon, Irvine, CA (US); Michelle Bayly, Aliso Viejo, CA (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 673 days.

(21) Appl. No.: 16/732,882

(22) Filed: Jan. 2, 2020

(65) Prior Publication Data
US 2020/0139036 A1   May 7, 2020

Related U.S. Application Data

(63) Continuation of application No. 15/215,404, filed on Jul. 20, 2016, now Pat. No. 10,549,023, which is a
(Continued)

(51) Int. Cl.
*A61M 1/28* (2006.01)
*A61M 1/16* (2006.01)

(52) U.S. Cl.
CPC ............ *A61M 1/28* (2013.01); *A61M 1/1696* (2013.01); *A61M 1/284* (2014.02); *A61M 1/288* (2014.02);
(Continued)

(58) Field of Classification Search
CPC ...... A61M 1/28; A61M 1/1696; A61M 1/284; A61M 1/288; A61M 2205/12; A61M 2205/3393; A61M 2205/75; A61M 1/14
See application file for complete search history.

(56) References Cited

U.S. PATENT DOCUMENTS 2,328,381 A   8/1943   Jaffe
3,707,967 A   1/1973   Kitrilakis et al.
(Continued)

FOREIGN PATENT DOCUMENTS

CN   1141006 A    1/1997
CN   1859936 A    11/2006
(Continued)

OTHER PUBLICATIONS

International Search Report PCT/US08/85062, dated Mar. 20, 2009, XCorporeal, Inc.
(Continued)

*Primary Examiner* — Lauren P Farrar
*Assistant Examiner* — Hamza A Darb
(74) *Attorney, Agent, or Firm* — Kilyk & Bowersox, P.L.L.C.

(57) ABSTRACT

Methods, systems, and kits are provided for performing hemodialysis, hemodiafiltration, and peritoneal dialysis on a portable machine suitable for both clinical and home use. Peritoneal dialysate can be flowed into and out of the peritoneal cavity, and can also be regenerated within the system, without the need for introducing fresh dialysate. Common hardware and software can be utilized for both peritoneal dialysis and other forms of dialysis such as hemodialysis, hemofiltration, and hemodiafiltration, allowing for facile transition between different dialysis modes using the same dialysis machine.

18 Claims, 12 Drawing Sheets

Related U.S. Application Data continuation of application No. 13/828,636, filed on Mar. 14, 2013, now Pat. No. 9,433,720.

(52) U.S. Cl.
CPC .. *A61M 2205/12* (2013.01); *A61M 2205/3393* (2013.01); *A61M 2205/75* (2013.01)

(56) References Cited

U.S. PATENT DOCUMENTS

| | | |
|---|---|---|
| 3,989,622 A | 11/1976 | Marantz et al. |
| 4,071,444 A | 1/1978 | Ash et al. |
| 4,141,836 A | 2/1979 | Schael |
| 4,172,794 A | 10/1979 | Sigdell |
| 4,190,047 A | 2/1980 | Jacobsen et al. |
| 4,213,859 A | 7/1980 | Smakman et al. |
| 4,247,393 A | 1/1981 | Wallace |
| 4,261,830 A | 4/1981 | Schael et al. |
| 4,311,587 A | 1/1982 | Nose et al. |
| 4,347,136 A | 8/1982 | Friesen et al. |
| 4,348,283 A | 9/1982 | Ash |
| 4,368,737 A | 1/1983 | Ash |
| 4,387,777 A | 6/1983 | Ash |
| 4,402,694 A | 9/1983 | Ash et al. |
| 4,403,984 A | 9/1983 | Ash et al. |
| 4,413,988 A | 11/1983 | Handt et al. |
| 4,464,172 A | 8/1984 | Lichtenstein |
| 4,469,593 A | 9/1984 | Ishihara et al. |
| 4,498,902 A | 2/1985 | Ash et al. |
| 4,559,039 A | 12/1985 | Ash et al. |
| 4,568,366 A | 2/1986 | Frederick et al. |
| 4,581,141 A | 4/1986 | Ash |
| 4,661,246 A | 4/1987 | Ash |
| 4,740,755 A | 4/1988 | Ogawa |
| 4,777,953 A | 10/1988 | Ash et al. |
| 4,854,322 A | 8/1989 | Ash et al. |
| 4,914,819 A | 4/1990 | Ash |
| 4,943,279 A | 7/1990 | Samiotes et al. |
| 4,995,268 A | 2/1991 | Ash et al. |
| 4,997,570 A | 3/1991 | Polaschegg |
| 5,002,054 A | 3/1991 | Ash et al. |
| 5,032,261 A | 7/1991 | Pyper |
| 5,100,554 A | 3/1992 | Polaschegg |
| 5,114,580 A | 5/1992 | Ahmad et al. |
| 5,147,613 A | 9/1992 | Heilmann et al. |
| 5,198,335 A | 3/1993 | Sekikawa et al. |
| 5,211,643 A | 5/1993 | Reinhardt et al. |
| 5,230,341 A | 7/1993 | Polaschegg |
| 5,277,820 A | 1/1994 | Ash |
| 5,295,505 A | 3/1994 | Polaschegg et al. |
| 5,304,349 A | 4/1994 | Polaschegg |
| 5,308,315 A | 5/1994 | Khuri et al. |
| 5,322,519 A | 6/1994 | Ash |
| 5,385,005 A | 1/1995 | Ash |
| 5,405,315 A | 4/1995 | Khuri et al. |
| 5,445,630 A | 8/1995 | Richmond |
| 5,460,493 A | 10/1995 | Deniega et al. |
| D355,816 S | 12/1995 | Ash |
| 5,476,444 A | 12/1995 | Keeling et al. |
| D370,531 S | 6/1996 | Ash et al. |
| 5,536,412 A | 7/1996 | Ash |
| 5,540,265 A | 7/1996 | Polaschegg et al. |
| 5,577,891 A | 11/1996 | Loughnane et al. |
| 5,580,460 A | 12/1996 | Polaschegg |
| 5,609,770 A | 3/1997 | Zimmerman et al. |
| 5,614,677 A | 3/1997 | Wamsiedler et al. |
| 5,616,305 A | 4/1997 | Mathieu |
| 5,624,551 A | 4/1997 | Baumann et al. |
| 5,632,897 A | 5/1997 | Mathieu |
| 5,698,083 A | 12/1997 | Glass |
| 5,711,883 A | 1/1998 | Folden et al. |
| 5,713,850 A | 2/1998 | Heilmann et al. |
| 5,725,773 A | 3/1998 | Polaschegg |
| 5,730,712 A | 3/1998 | Falkvall et al. |
| 5,782,796 A | 7/1998 | Din et al. |
| 5,794,669 A | 8/1998 | Polaschegg et al. |
| 5,858,186 A | 1/1999 | Glass |
| 5,868,933 A | 2/1999 | Patrick et al. |
| 5,882,516 A | 3/1999 | Gross et al. |
| 5,906,978 A | 5/1999 | Ash |
| 5,919,369 A | 7/1999 | Ash |
| 5,944,684 A | 8/1999 | Roberts et al. |
| 5,947,953 A | 9/1999 | Ash et al. |
| 5,989,438 A | 11/1999 | Fumiyama |
| 6,042,561 A | 3/2000 | Ash et al. |
| 6,156,007 A | 12/2000 | Ash |
| 6,190,349 B1 | 2/2001 | Ash et al. |
| 6,217,540 B1 | 4/2001 | Yazawa et al. |
| 6,234,989 B1 | 5/2001 | Brierton et al. |
| 6,254,567 B1 | 7/2001 | Treu et al. |
| 6,264,680 B1 | 7/2001 | Ash |
| 6,287,516 B1 | 9/2001 | Matson et al. |
| 6,303,036 B1 | 10/2001 | Collins et al. |
| 6,332,985 B1 | 12/2001 | Sherman et al. |
| 6,348,162 B1 | 2/2002 | Ash |
| 6,409,699 B1 | 6/2002 | Ash |
| 6,471,872 B2 | 10/2002 | Kitaevich et al. |
| 6,497,675 B1 | 12/2002 | Davankov |
| 6,551,513 B2 | 4/2003 | Nikaido et al. |
| 6,554,789 B1 | 4/2003 | Brugger et al. |
| 6,565,749 B1 | 5/2003 | Hou et al. |
| 6,572,576 B2 | 6/2003 | Brugger et al. |
| 6,572,641 B2 | 6/2003 | Brugger et al. |
| 6,579,253 B1 | 6/2003 | Burbank et al. |
| 6,579,460 B1 | 6/2003 | Willis et al. |
| 6,582,385 B2 | 6/2003 | Burbank et al. |
| 6,589,482 B1 | 7/2003 | Burbank et al. |
| 6,595,943 B1 | 7/2003 | Burbank |
| 6,623,470 B2 | 9/2003 | Munis et al. |
| 6,627,164 B1 | 9/2003 | Wong |
| 6,638,477 B1 | 10/2003 | Treu et al. |
| 6,638,478 B1 | 10/2003 | Treu et al. |
| 6,649,063 B2 | 11/2003 | Brugger et al. |
| 6,653,841 B1 | 11/2003 | Koerdt et al. |
| 6,673,314 B1 | 1/2004 | Burbank et al. |
| 6,702,561 B2 | 3/2004 | Stillig et al. |
| 6,730,266 B2 | 5/2004 | Matson et al. |
| 6,743,193 B2 | 6/2004 | Brugger et al. |
| 6,764,460 B2 | 7/2004 | Dolecek et al. |
| 6,802,821 B2 | 10/2004 | Jacobsen et al. |
| 6,818,196 B2 | 11/2004 | Wong |
| 6,830,553 B1 | 12/2004 | Burbank et al. |
| 6,841,172 B1 | 1/2005 | Ash |
| 6,852,090 B2 | 2/2005 | Burbank et al. |
| 6,872,346 B2 | 3/2005 | Stillig |
| 6,878,283 B2 | 4/2005 | Thompson |
| 6,911,007 B2 | 6/2005 | Nier et al. |
| 6,923,782 B2 | 8/2005 | O'Mahony et al. |
| 6,955,655 B2 | 10/2005 | Burbank et al. |
| 6,958,049 B1 | 10/2005 | Ash |
| 6,960,179 B2 | 11/2005 | Gura |
| 6,960,328 B2 | 11/2005 | Bortun et al. |
| 6,979,309 B2 | 12/2005 | Burbank et al. |
| 6,989,101 B2 | 1/2006 | Cumberland et al. |
| 7,004,924 B1 | 2/2006 | Brugger et al. |
| 7,033,498 B2 | 4/2006 | Wong |
| 7,040,142 B2 | 5/2006 | Burbank |
| 7,087,033 B2 | 8/2006 | Brugger et al. |
| 7,101,519 B2 | 9/2006 | Wong |
| 7,112,273 B2 | 9/2006 | Weigel et al. |
| 7,115,095 B2 | 10/2006 | Eigler et al. |
| 7,135,156 B2 | 11/2006 | Hai et al. |
| 7,144,386 B2 | 12/2006 | Korkor et al. |
| 7,147,613 B2 | 12/2006 | Burbank et al. |
| 7,169,303 B2 | 1/2007 | Sullivan et al. |
| 7,175,809 B2 | 2/2007 | Gelfand et al. |
| 7,214,312 B2 | 5/2007 | Brugger et al. |
| 7,226,538 B2 | 6/2007 | Brugger et al. |
| 7,241,272 B2 | 7/2007 | Karoor et al. |
| 7,252,767 B2 | 8/2007 | Bortun et al. |
| 7,267,658 B2 | 9/2007 | Treu et al. |
| 7,273,465 B2 | 9/2007 | Ash |
| 7,276,042 B2 | 10/2007 | Polaschegg et al. |
| 7,300,413 B2 | 11/2007 | Burbank et al. |

(56) References Cited

U.S. PATENT DOCUMENTS

| | | | |
|---|---|---|---|
| 7,303,683 B2 | 12/2007 | Cumberland | |
| 7,309,323 B2 | 12/2007 | Gura et al. | |
| 7,337,674 B2 | 3/2008 | Burbank et al. | |
| 7,338,460 B2 | 3/2008 | Burbank et al. | |
| 7,347,849 B2 | 3/2008 | Brugger et al. | |
| 7,494,590 B2 | 2/2009 | Felding et al. | |
| 7,614,506 B2 | 11/2009 | Mitchell et al. | |
| 7,615,152 B2 | 11/2009 | Tanner et al. | |
| 7,736,507 B2 | 6/2010 | Wong | |
| 7,901,376 B2 | 3/2011 | Steck et al. | |
| 7,922,008 B2 | 4/2011 | Bahm et al. | |
| 8,202,428 B2 | 6/2012 | Heilmann et al. | |
| 8,303,807 B2 | 11/2012 | Zhang | |
| 8,512,553 B2 | 8/2013 | Cicchello et al. | |
| 9,433,720 B2 | 9/2016 | Updyke et al. | |
| 10,549,023 B2 * | 2/2020 | Updyke | A61M 1/288 |
| 2001/0037964 A1 | 11/2001 | Won et al. | |
| 2002/0028155 A1 | 3/2002 | Dolecek et al. | |
| 2002/0045851 A1 * | 4/2002 | Suzuki | A61M 5/44 |
| | | | 604/113 |
| 2002/0068364 A1 | 6/2002 | Arai et al. | |
| 2002/0085951 A1 | 7/2002 | Gelfand et al. | |
| 2002/0112609 A1 * | 8/2002 | Wong | B01J 20/20 |
| | | | 96/135 |
| 2003/0000884 A1 | 1/2003 | Hamlin et al. | |
| 2003/0048185 A1 | 3/2003 | Citrenbaum, et al. | |
| 2003/0097086 A1 | 5/2003 | Gura | |
| 2003/0098276 A1 | 5/2003 | Carlson | |
| 2003/0114787 A1 | 6/2003 | Gura | |
| 2003/0126910 A1 | 7/2003 | Burbank | |
| 2004/0019312 A1 * | 1/2004 | Childers | A61M 1/28 |
| | | | 604/4.01 |
| 2004/0019320 A1 | 1/2004 | Childers et al. | |
| 2004/0050789 A1 | 3/2004 | Ash | |
| 2004/0082903 A1 | 4/2004 | Micheli | |
| 2004/0084358 A1 | 5/2004 | O'Mahony et al. | |
| 2004/0164006 A1 | 8/2004 | Brown et al. | |
| 2004/0167465 A1 | 8/2004 | Mihai et al. | |
| 2005/0000883 A1 | 1/2005 | Kouters et al. | |
| 2005/0006296 A1 | 1/2005 | Sullivan et al. | |
| 2005/0020959 A1 | 1/2005 | Brugger et al. | |
| 2005/0044950 A1 | 3/2005 | Kwon et al. | |
| 2005/0061740 A1 | 3/2005 | Felding et al. | |
| 2005/0070837 A1 | 3/2005 | Ferrarini et al. | |
| 2005/0131332 A1 | 6/2005 | Kelly et al. | |
| 2005/0133439 A1 | 6/2005 | Blickhan | |
| 2005/0236330 A1 | 10/2005 | Nier et al. | |
| 2006/0122552 A1 | 6/2006 | O'Mahony | |
| 2006/0195064 A1 | 8/2006 | Plahey et al. | |
| 2007/0112297 A1 | 5/2007 | Plahey et al. | |
| 2007/0158267 A1 | 7/2007 | Micheli | |
| 2007/0161113 A1 | 7/2007 | Ash | |
| 2007/0173979 A1 | 7/2007 | Harkanyi et al. | |
| 2007/0179431 A1 | 8/2007 | Roberts et al. | |
| 2007/0213654 A1 | 9/2007 | Lundtveit et al. | |
| 2007/0213665 A1 | 9/2007 | Curtin et al. | |
| 2007/0278141 A1 | 12/2007 | Patera et al. | |
| 2008/0041136 A1 | 2/2008 | Kopelman et al. | |
| 2008/0041792 A1 | 2/2008 | Crnkovich et al. | |
| 2008/0164214 A1 | 7/2008 | Lerner et al. | |
| 2008/0200869 A1 | 8/2008 | Bedingfield | |
| 2008/0214981 A1 | 9/2008 | Delnevo et al. | |
| 2008/0215247 A1 | 9/2008 | Tonelli et al. | |
| 2008/0230450 A1 | 9/2008 | Burbank et al. | |
| 2008/0249377 A1 | 10/2008 | Molducci et al. | |
| 2008/0253427 A1 | 10/2008 | Kamen et al. | |
| 2008/0258735 A1 | 10/2008 | Quackenbush et al. | |
| 2009/0007862 A1 | 1/2009 | Nakamura et al. | |
| 2009/0012447 A1 | 1/2009 | Huitt et al. | |
| 2009/0012460 A1 | 1/2009 | Steck et al. | |
| 2009/0012655 A1 | 1/2009 | Kienman et al. | |
| 2009/0024070 A1 | 1/2009 | Gelfand et al. | |
| 2009/0076434 A1 | 3/2009 | Mischelevich et al. | |
| 2009/0078622 A1 | 3/2009 | Zhang et al. | |
| 2009/0095679 A1 | 4/2009 | Demers et al. | |
| 2009/0101552 A1 | 4/2009 | Fulkerson et al. | |
| 2009/0101577 A1 | 4/2009 | Fulkerson et al. | |
| 2009/0113335 A1 | 4/2009 | Sandoe et al. | |
| 2009/0114037 A1 | 5/2009 | Smith | |
| 2009/0120864 A1 | 5/2009 | Fulkerson et al. | |
| 2009/0124963 A1 | 5/2009 | Hogard et al. | |
| 2009/0127193 A1 | 5/2009 | Updyke et al. | |
| 2009/0173682 A1 * | 7/2009 | Robinson | A61M 1/367 |
| | | | 210/240 |
| 2009/0187138 A1 | 7/2009 | Lundtveit et al. | |
| 2009/0188854 A1 | 7/2009 | Farrelly et al. | |
| 2009/0206023 A1 | 8/2009 | Rohde et al. | |
| 2009/0218288 A1 | 9/2009 | Karoor et al. | |
| 2009/0264812 A1 | 10/2009 | Micheli | |
| 2009/0312694 A1 | 12/2009 | Bedingfield et al. | |
| 2009/0314707 A1 | 12/2009 | Karoor et al. | |
| 2010/0010428 A1 | 1/2010 | Yu et al. | |
| 2010/0010429 A1 | 1/2010 | Childers et al. | |
| 2010/0010430 A1 | 1/2010 | Micheli | |
| 2010/0078387 A1 | 4/2010 | Wong | |
| 2010/0100027 A1 | 4/2010 | Schilthuizen et al. | |
| 2010/0114012 A1 | 5/2010 | Sandford et al. | |
| 2010/0116048 A1 | 5/2010 | Fulkerson et al. | |
| 2010/0116740 A1 | 5/2010 | Fulkerson et al. | |
| 2010/0121246 A1 | 5/2010 | Peters et al. | |
| 2010/0137782 A1 * | 6/2010 | Jansson | A61M 1/281 |
| | | | 604/28 |
| 2010/0140149 A1 | 6/2010 | Fulkerson et al. | |
| 2010/0179464 A1 | 7/2010 | Smith | |
| 2010/0184198 A1 | 7/2010 | Joseph et al. | |
| 2010/0217181 A1 | 8/2010 | Roberts et al. | |
| 2010/0230346 A1 | 9/2010 | Eisen | |
| 2010/0234786 A1 | 9/2010 | Fulkerson et al. | |
| 2010/0252490 A1 | 10/2010 | Fulkerson et al. | |
| 2010/0282834 A1 | 11/2010 | Devergne et al. | |
| 2010/0312172 A1 | 12/2010 | Hoffman | |
| 2010/0312174 A1 | 12/2010 | Hoffman | |
| 2010/0314314 A1 | 12/2010 | Ding et al. | |
| 2010/0331754 A1 | 12/2010 | Fulkerson et al. | |
| 2011/0000832 A1 | 1/2011 | Kelly et al. | |
| 2011/0017665 A1 | 1/2011 | Updkye et al. | |
| 2011/0054378 A1 | 3/2011 | Fulkerson | |
| 2011/0071465 A1 | 3/2011 | Wang et al. | |
| 2011/0093294 A1 | 4/2011 | Elahi et al. | |
| 2011/0155667 A1 | 6/2011 | Charest et al. | |
| 2011/0160649 A1 | 6/2011 | Pan | |
| 2011/0166507 A1 | 7/2011 | Childers et al. | |
| 2011/0171713 A1 | 7/2011 | Bluchel et al. | |
| 2011/0184340 A1 | 7/2011 | Tan et al. | |
| 2011/0272337 A1 | 11/2011 | Palmer | |
| 2011/0297593 A1 | 12/2011 | Kelly et al. | |
| 2011/0297598 A1 | 12/2011 | Lo et al. | |
| 2011/0297599 A1 | 12/2011 | Lo et al. | |
| 2011/0303588 A1 | 12/2011 | Kelly et al. | |
| 2011/0303590 A1 | 12/2011 | Childers et al. | |
| 2011/0303598 A1 | 12/2011 | Lo et al. | |
| 2011/0315611 A1 | 12/2011 | Fulkerson et al. | |
| 2012/0031826 A1 | 2/2012 | Childers et al. | |
| 2012/0037550 A1 | 2/2012 | Childers et al. | |
| 2012/0043279 A1 | 2/2012 | Kelly et al. | |
| 2012/0073365 A1 | 3/2012 | Fulkerson et al. | |
| 2012/0090706 A1 | 4/2012 | Fulkerson et al. | |
| 2012/0103885 A1 | 5/2012 | Robinson et al. | |
| 2012/0172736 A1 | 7/2012 | Zhang et al. | |
| 2012/0204968 A1 | 8/2012 | Fulkerson et al. | |
| 2012/0220926 A1 | 8/2012 | Soykan et al. | |
| 2012/0248017 A1 | 10/2012 | Beiriger et al. | |
| 2012/0271227 A1 | 10/2012 | Roberts et al. | |
| 2012/0273354 A1 | 11/2012 | Orhan et al. | |
| 2012/0280154 A1 | 11/2012 | Smith | |
| 2013/0004593 A1 | 1/2013 | Kloeffel et al. | |
| 2013/0008852 A1 | 1/2013 | Eisen | |
| 2014/0263062 A1 | 9/2014 | Updyke et al. | |
| 2016/0038666 A1 | 2/2016 | Kelly et al. | |

FOREIGN PATENT DOCUMENTS

| | | |
|---|---|---|
| CN | 101175514 A | 5/2008 |
| CN | 102307650 A | 1/2012 |

(56) References Cited

FOREIGN PATENT DOCUMENTS

| EP | 0498382 A1 | 8/1992 |
| EP | 2320969 A1 | 5/2011 |
| WO | 9520985 | 8/1995 |
| WO | WO 2009/073567 A1 | 6/2009 |
| WO | 2010024963 A1 | 3/2010 |
| WO | 2014159918 A2 | 10/2014 |

OTHER PUBLICATIONS

International Search Report PCT/US10/29500, dated Jul. 10, 2010, XCorporeal, Inc.
Office Action for Chinese Patent Application No. 201480015423.9, issued by the Chinese State Intellectual Property Office (SIPO), dated May 24, 2016, including search report and English-language translation, 26 pages.
Final Office Action for U.S. Appl. No. 13/828,240, dated Jan. 12, 2016, including Form PTO-892.
Non-Final Office Action for U.S. Appl. No. 14/958,335, dated Jan. 7, 2016, including Form PTO-892.
Non-Final Office Action for commonly owned U.S. Appl. No. 13/828,240, dated Jul. 27, 2015, including Form PTO-892.
International Search Report and Written Opinion issued in corresponding International Patent Application No. PCT/US2014/025450 dated Feb. 9, 2015 (19 pages).
Communication Relating to the Results of the Partial International Search issued in corresponding International Patent Application No. PCT/US2014/025450 dated Sep. 25, 2014 (8 pages).
Office Action for Chinese Patent Application No. 201480015423.9, issued by the Chinese State Intellectual Property Office (SIPO), dated Nov. 17, 2016, including English-language translation, 10 pages.
Office Action for Chinese Patent Application No. 201710619365.6, issued by the China National Intellectual Property Administration (CNIPA), dated May 27, 2019, including English-language translation, 6 pages.

* cited by examiner

UNIVERSAL PORTABLE ARTIFICIAL KIDNEY FOR HEMODIALYSIS AND PERITONEAL DIALYSIS

CROSS-REFERENCE TO RELATED APPLICATIONS

This application is a continuation application of U.S. patent application Ser. No. 15/215,404, filed Jul. 20, 2016, now U.S. Pat. No. US 10,549,023 B2, issued Feb. 4, 2020, which in-turn is a continuation of U.S. patent application Ser. No. 13/828,636, filed Mar. 14, 2013, now U.S. Pat. No. US 9,433,720 B2, issued Sep. 6, 2016, all of which are incorporated herein by reference in their entireties.

FIELD OF THE INVENTION

The present invention relates to kidney replacement dialysis and in particular to materials and methods for performing peritoneal dialysis, as well as other modes of dialysis.

BACKGROUND OF THE INVENTION

Dialysis is an important treatment regimen for a variety of chronic diseases. Dialysis to support a patient, whose renal function has decreased to the point where the kidneys no longer sufficiently function, is well known. To meet the need for regular care, patients often travel to hospitals or dialysis centers. A nurse or patient care technician usually oversees dialysis treatment sessions at such centers.

With the advent of more affordable equipment, home dialysis is increasingly an option for many dialysis patients, who find it offers them greater privacy, flexibility of scheduling, and overall comfort. Home provision of hemodialysis can also be advantageous to health care providers, because it does not require the nursing, equipment, and overhead costs of standard in-center care. Government and private insurers also stand to benefit, because home hemodialysis tends to lower coverage costs over the long term.

Two principal dialysis methods are utilized, hemodialysis, and peritoneal dialysis. In hemodialysis, the patient's blood is passed through an artificial kidney dialysis machine. A membrane in the machine acts as an artificial kidney for cleansing the blood. Extracorporeal treatment usually involves special machinery and a visit to a center, such as a hospital or an out-patient facility, where the treatment is performed.

To overcome some of the disadvantages associated with hemodialysis, peritoneal dialysis was developed. Peritoneal dialysis is a medical procedure for removing toxins from the blood and takes advantage of the semi-permeable membrane surrounding the walls of the abdomen or peritoneal cavity. During a peritoneal procedure, a solution is introduced into the patient's abdomen, where it remains for up to several hours, removing blood toxins via osmotic transfer through the peritoneal membrane. At completion of the procedure, the solution is drained from the body along with the toxins. In continuous ambulatory peritoneal dialysis, a dialysis solution is introduced into the peritoneal cavity utilizing a catheter, normally placed into position by a surgical placement physician. An exchange of solutes between the dialysate and the blood is achieved by diffusion.

During the course of kidney disease, the needs and capabilities of a patient can change with respect to dialysis. While at times hemodialysis may be the appropriate treatment, at other times peritoneal dialysis may be the best treatment. For example, the peritoneum of a patient undergoing peritoneal dialysis may degenerate overtime so that it can no longer serve as a sufficient membrane for discharging toxins, solutes, and excess fluids. The patient would then likely need to be switched to hemodialysis if kidney transplantation is not available. For greater flexibility and cost-savings, it would be advantageous to be able to use a common machine to perform hemodialysis or peritoneal dialysis, depending on the patient's dialysis requirements.

Accordingly, there is a need for materials and methods for utilizing a dialysis machine interchangeably between a peritoneal dialysis mode and a hemodialysis mode.

SUMMARY OF THE PRESENT INVENTION

A feature of the present invention is to provide methods and corresponding systems for carrying out peritoneal dialysis, which are also compatible with hemodialysis, hemofiltration, and hemodiafiltration.

Another feature of the present invention is to provide methods and corresponding systems for performing peritoneal dialysis, which allow for transition between different modes of dialysis using a common dialysis machine.

Yet another feature of the present invention is to provide methods and corresponding systems that enable the performance of both peritoneal dialysis and associated dialysate regeneration.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description below and appended claims.

To achieve these and other advantages, and in accordance with the purposes of the present invention, as embodied and broadly described herein, the present invention relates to a method of performing peritoneal dialysis. Dialysate can be flowed through a manifold along a first flow path and into a dialysate reservoir. The dialysate can be weighed in the dialysate reservoir. The dialysate can be flowed out of the reservoir, through the manifold along a second flow path, and into a peritoneal cavity. The dialysate can be flowed out of the peritoneal cavity, through the manifold along a third flow path, and into a drain reservoir. The dialysate can be weighed in the drain reservoir. The dialysate can be flowed out of the drain reservoir and through the manifold along a fourth flow path.

Peritoneal dialysis systems configured to carry out the methods of the present invention are also part of the present invention. For example, a peritoneal dialysis system is provided that can include one or more of a manifold, a dialysis machine in operable communication with the manifold and configured to pump the dialysate through the first, second, third, and fourth flow paths, a dialysate reservoir in fluid communication with the manifold, a drain reservoir in fluid communication with the manifold, a scale configured to weigh at least one of the dialysate reservoir and the drain reservoir, and a heater configured to heat dialysate in the dialysate reservoir. Kits for carrying out the dialysis methods are provided by the present invention, which can include one or more components for carrying out the dialysis methods and/or forming the dialysis systems.

In accordance with the present invention, another method of performing peritoneal dialysis is provided. Dialysate can be flowed in a dialysate circuit through a manifold along a first flow path that includes a sorbent cartridge, and into a dialysate reservoir. The dialysate can be flowed in the dialysate circuit, out of the dialysate reservoir, and through the manifold along a second flow path. The dialysate can be flowed from the second flow path, across at least one filter, and into a peritoneum circuit. The dialysate in the peritoneum circuit can be flowed into a peritoneal cavity. The dialysate can be flowed out of the peritoneal cavity, through the peritoneum circuit, across the filter, and back into the dialysate circuit. The dialysate can be flowed through the manifold, along a third flow path that includes the sorbent cartridge, and back into the dialysate reservoir.

In accordance with the present invention, a further method of performing peritoneal dialysis is provided. A first dialysate can be flowed in a peritoneum circuit along a first flow path through a manifold. A second dialysate can be flowed in a regeneration circuit along a second flow path through the manifold and a sorbent cartridge, and into a dialysate reservoir. The second dialysate can be flowed out of the dialysate reservoir along a third flow path through a first lumen of a dialyzer. The first dialysate can be flowed through a second lumen of the dialyzer, which is separated from the first lumen by at least one semipermeable membrane. The first dialysate can be flowed into a peritoneal cavity. The first dialysate can be flowed out of the peritoneal cavity. The present invention provides methods of, and components, machines, and systems for performing hemodialysis, hemofiltration, and hemodiafiltration, as well as peritoneal dialysis.

It is to be understood that both the foregoing general description and the following detailed description are exemplary and explanatory only and are intended to provide a further explanation of the present invention, as claimed.

BRIEF DESCRIPTION OF THE DRAWINGS

The invention may be more fully understood with reference to the accompanying drawings. The drawings are intended to illustrate, not limit, the present teachings.

DETAILED DESCRIPTION OF THE PRESENT INVENTION

Figure 1:
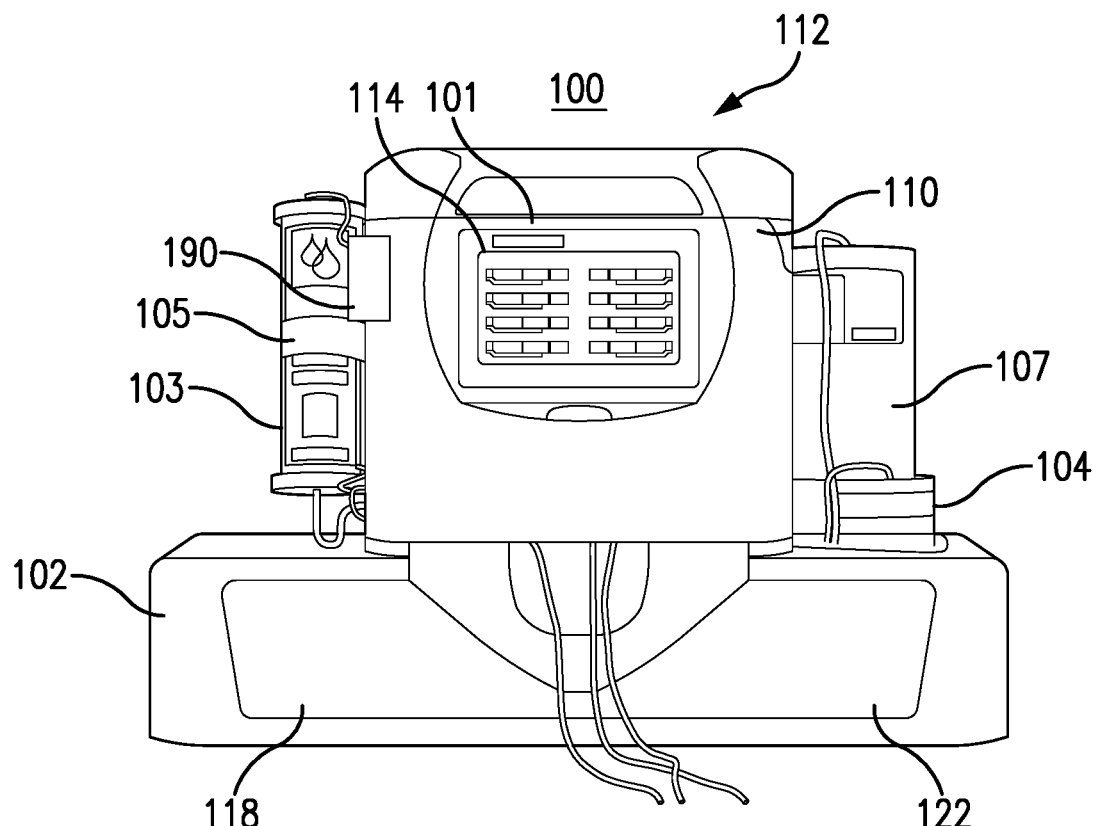
FIG. 1 is a front view of a dialysis system in accordance with the present invention.

In accordance with the present invention, a universal system is provided that can be used for hemodialysis or peritoneal dialysis. Methods of performing hemodialysis and peritoneal dialysis are also provided. In the method of performing peritoneal dialysis, dialysate can be flowed through a manifold along a first flow path and into a dialysate reservoir. The dialysate can be weighed in the dialysate reservoir. The dialysate can be flowed out of the reservoir, along a second flow path through the manifold, and into a peritoneal cavity. The dialysate can have any suitable dwell time in the peritoneal cavity, for example, less than about 5.0 minutes, from about 5.0 minutes to about 5.0 days, from about 30 minutes to about 2.0 days, from about 1.0 hour to about 1.0 day, from about 2.0 hours to about 18 hours, from about 3.0 hours to about 16 hours, from about 4.0 hours to about 12 hours, from about 6.0 hours to about 10 hours, or for any other intervening time span. The dialysate can be flowed out of the peritoneal cavity, along a third flow path through the manifold, and into a drain reservoir. The dialysate can be weighed in the drain reservoir. The dialysate can be flowed out of the drain reservoir and along a fourth flow path through the manifold. The dialysis methods of the present invention can be performed continuously or at prescribed intervals, which may be variable or constant. For example, dialysis sessions can be separated by about 30 minutes, by about 1.0 hour, by about 3.0 hours, by about 6.0 hours, by about 12 hours, by about 18 hours, by about 1.0 day, by about 2.0 days, by about 3.0 days, by about 4.0 days, by about 1.0 week, or by about 2.0 weeks or more. The dialysate can be heated in the dialysate reservoir using one or more heater and thermistor. The dialysate reservoir and the drain reservoir can be weighed using a common scale or separated scales. At least one of ultrafiltration volume and ultrafiltration rate can be determined based on a difference of the weights obtained from the weighing the clean dialysate in the dialysate reservoir and weighing the waste dialysate in the drain reservoir.

The dialysate in the system can be flowed actively, passively, or by a combination thereof. A passive flow can be achieved by using gravity and/or a pressure differential. An active flow can be achieved by using one or more pump of any suitable design. Accordingly, the dialysate can be flowed by using at least one pump. The at least one pump can include at least one peristaltic pump, at least one positive displacement pump, at least one negative displacement pump, at least one diaphragm pump, an impeller, a pumping chamber, or any combination thereof. The at least one pump can include a first pump configured to control dialysate flow in one of the flow paths and a second pump configured to control dialysate in another of the flow paths. The at least one pump can include a pump configured to control dialysate flow in more than one of the flow paths. The pump can be configured to run in either direction. The flow paths described herein can include flow in one direction, flow in an opposite direction, flow in either direction, or flow in both directions along a given flow path.

Any of the methods of the present invention can include measurement of any parameter, for example, pressure, temperature, conductivity, pH, solute concentration, solvent concentration, microorganisms, toxins, and the like. Any of the methods, machines, and systems of the present invention can include one or more elements for controlling one or more of such parameters. The methods can include detecting a condition, for example, the presence of air in the system, or leaks into or out of the system. For example, a pressure of the dialysate can be measured in at least one of the second and third flow paths. The flow of dialysate into and/or out of the peritoneal cavity can be adjusted to control the dialysate pressure and keep it below a pre-determined value, for example, a value determined to be deleterious to the peritoneum.

The methods of the invention can be repeated any desired number of times, for example, in accordance with a particular dialysis prescription, to achieve a desired result. Desired results can include, for example, removal of a particular amount or percentage of toxins, and/or an exchange of solvent. The method can be repeated by flowing a fresh supply of dialysate through the first flow path after flowing the dialysate through the fourth flow path. The method can include flowing a fresh supply of dialysate through a fifth flow path and into the dialysate reservoir after flowing the dialysate through the fourth flow path. The fresh supply of dialysate can differ in composition from the dialysate originally flowed through the manifold and into the dialysate reservoir. Such a difference in composition is consistent with the practice in the art of a "last bag" approach in peritoneal dialysis, for example, the use of a different dialysate formulation after a number of cycles of dialysate flow in and out of the peritoneal cavity.

Any method of the present invention can be practiced using any suitable dialysis machine. Accordingly, the method can further include engaging the manifold with a dialysis machine configured to carry out the method. The manifold can be placed in fluid communication with a supply of dialysate. The method can further include attaching one or more other disposables to the dialysis machine, such as dialyzers, filters, plastic tubing, sorbent cartridges, reservoir liners, ammonia sensors, priming fluid sources, electrolyte sources, osmotic agent sources, and the like. The manifold and one or more of these other disposables can be provided preassembled, partially or completely, for example, as part of a kit. The components in the kit can be preassembled (connected), separate, or both. Components can be coded, for example, using colors, letters, numbers, barcodes, RFID tags, or a combination thereof, to aid in the assembly of the components with a dialysis machine to form a dialysis system. One or more components of the kit can be disposable and/or reusable.

Any suitable manifold can be used in accordance with the methods and systems of the present invention. The manifold can be disposable and/or reusable. The manifold can be provided with any suitable or desired design that permits a method of the present invention to be performed. The manifold can be provided with a shape or other physical or geometric parameter that allows the manifold to engage a suitable dialysis machine, for example, in only one orientation. For example, the manifold can have an H-shaped or I-shaped design. Such a design can include first and second transoms connected by a central trunk. The first transom can have a first edge, and second and third edges that are substantially parallel to the first edge. The trunk can be substantially perpendicular and adjacent to the first transom. The second transom can have a fourth edge, and fifth and sixth edges that are substantially parallel to the first, second, and third edges. The second transom can be substantially perpendicular and adjacent to the trunk and substantially parallel to the first transom. One or more conduits, that is, internal passageways, can be integrated into the manifold along with one or more ports to allow for fluid communication with other conduits or fluid passageways external to the manifold. The manifold can be provided with any suitable number of conduits, that is, interior passage ways, for carrying out the method. For example, the manifold can include at least four manifold conduits and each flow path can include at least one manifold conduit not included by the other three flow paths. The manifold can contain at least two manifold conduits and at least two of the four flow paths can include a common manifold conduit. Any desirable type or number of additional elements can be included in the manifold, for example, pump tubes, valves, pressure chambers, pressure sensors, flow rate sensors, conductivity sensors, air detectors, blood detectors, toxin detectors, actuators, thermistors, heaters, conductivity meters, pH meters, components thereof, and combinations thereof.

U.S. Patent Application Publication Nos. US 2012/0280154 A1 and US 2010/0179464 A1, which are incorporated herein by reference in their entireties, describe valves and other elements that can be used in accordance with the present invention. US 2012/0204968 A1, which is incorporated herein by reference in its entirety, describes priming methods and other elements that can be used in accordance with the present invention. US 2012/0103885 A1, US 2012/0090706 A1, US 2010/0116740 A1, and US 2009/0173682 A1, which are incorporated herein by reference in their entireties, describe manifolds, ultrafiltration control means, and other elements that can be used in accordance with the present invention. US 2010/0331754 A1, 2009/0101577 A1, and US 2009/0076434 A1, which are incorporated herein by reference in their entireties, describe pressure measurements, volume control, ultrafiltration control, and other elements that can be used in accordance with the present invention. US 2010/0252490 A1, which is incorporated herein by reference in its entirety, describes a dialysate reservoir and other elements that can be used in accordance with the present invention. US 2010/0234786 A1, which is incorporated herein by reference in its entirety, describes a disconnection monitor and other elements that can be used in accordance with the present invention. US 2010/0184198 A1, which is incorporated herein by reference in its entirety, describes a method of ammonia removal and other elements that can be used in accordance with the present invention. US 2011/0315611 A1, US 2011/0054378 A1, US 2010/0140149 A1, and US 2009/0101552 A1, which are incorporated herein by reference in their entireties, describe a manifold, dialysis machine, dialysis system, and other elements that can be used in accordance with the present invention. US 2012/0073365 A1, US 2010/0116048 A1, and US 2009/0114037 A1, which are incorporated herein by reference in their entireties, describe flow meters and other elements that can be used in accordance with the present invention.

Peritoneal dialysis systems configured to carry out the methods of the present invention are also part of the present invention. For example, a peritoneal dialysis system is provided that can include one or more of a manifold, a dialysis machine in operable communication with the manifold and configured to pump the dialysate through the first, second, third, and fourth flow paths, a dialysate reservoir in fluid communication with the manifold, a drain reservoir in fluid communication with the manifold, a scale configured to weigh at least one of the dialysate reservoir and the drain reservoir, and a heater configured to heat dialysate in the dialysate reservoir. Kits for carrying out the dialysis methods are provided by the present invention, which can include one or more components for carrying out the dialysis methods and forming the dialysis systems.

Another method of performing peritoneal dialysis is provided by the present invention, wherein dialysate can be flowed in a dialysate circuit through a manifold along a first flow path that includes a sorbent cartridge, and into a dialysate reservoir. The dialysate can be flowed in the dialysate circuit out of the dialysate reservoir and through the manifold along a second flow path. The dialysate can be flowed from the second flow path, across at least one filter, and into a peritoneum circuit. The dialysate in the peritoneum circuit can be flowed into a peritoneal cavity. The dialysate can be maintained in the peritoneal cavity for a suitable dwell time. The dialysate can be flowed out of the peritoneal cavity through the peritoneum circuit, across the filter, and back into the dialysate circuit. The dialysate can be flowed through the manifold along a third flow path that includes the sorbent cartridge, and back into the dialysate reservoir. Any suitable filter can be used. The filter can be a dialyzer and/or a dialysis membrane. The filter can be a bacterial filter. For example, any of the bacterial filters described in U.S. Pat. Nos. 4,311,587, 4,347,136, 4,568,366, 5,868,933, 6,565,749 B2, U.S. Pat. No. 6,989,101 B2, U.S. Pat. No. 7,303,683 B2, U.S. Pat. No. 7,614,506 B2, U.S. Pat. No. 7,615,152 B2, and U.S. Pat. No. 7,922,008 B2 can be used, and all of these patents are incorporated herein by reference in their entireties. The bacterial filters described in U.S. Patent Application Publications Nos. 2001/0037964 A1, US 2003/0000884 A1, US 2003/0098276 A1, US 2004/0164006, US 2005/0000883 A1, US 2007/0278141 A1, US 2008/0164214 A1, and US 2009/0188854 A1 can be used, all of these publications are incorporated herein by reference in their entireties.

The method can include heating the dialysate in the dialysate reservoir. The method can include weighing the dialysate in the reservoir, for example, before the dialysate is flowed into the peritoneum, after the dialysate is returned to the dialysate reservoir, or both. At least one of ultrafiltration volume and ultrafiltration rate can be determined based on a difference of weights obtained from the weighing the dialysate before and after the dialysate has resided in the peritoneal cavity.

Any suitable manifold described herein or otherwise known or compatible can be used in the methods of the present invention. The manifold can contain at least three manifold conduits and each flow path can include at least one manifold conduit not included by the other three flow paths. The manifold can contain at least two manifold conduits and at least two of the three flow paths can share a common manifold conduit. The third flow path can share at least one common conduit with both the first and second flow paths, and the first and second flow paths can include no conduits in common.

The dialysate can be flowed using at least one pump. The at least one pump can include at least one peristaltic pump, another pump described herein, or any other suitable pump. The at least one pump can include a pump configured to control dialysate flow in more than one of the flow paths. The method can include measuring for the presence of air, and if air is detected, can trigger an alarm or other warning. The pressure of the dialysate can be measured in at least one of the second and third flow paths. The flow of dialysate into and/or out of the peritoneal cavity can be adjusted to control the dialysate pressure to keep it maintained below a pre-determined value. The method can be repeated by flowing dialysate from the dialysate reservoir through the second flow path after returning the dialysate through the third flow path to the dialysate reservoir. At least one filter can be used, for example, at least one dialyzer, or any other filter known or described herein, or any filter compatible with the method. The flow of dialysate in the second flow path can be split between at least two different branch lines before passing across the at least one filter. Any suitable manifold, machine, or system described herein, or otherwise known, or otherwise compatible, can be used to carry out the method. The manifold can be engaged with a dialysis machine configured to carry out the method. The manifold can be placed in fluid communication with a supply of dialysate.

A peritoneal dialysis system configured to perform the peritoneal dialysis methods described herein, is provided. The system can contain one or more of a manifold, a dialysis machine in operable communication with the manifold and configured to pump the dialysate through the first, second, and third flow paths, a dialysate reservoir in fluid communication with the manifold, a filter in fluid communication with the manifold, a sorbent cartridge in fluid communication with the manifold, a scale configured to weigh the dialysate reservoir, and a heater configured to heat dialysate in the dialysate reservoir.

A further method of performing peritoneal dialysis is provided by the present invention. A first dialysate can be flowed in a peritoneum circuit along a first flow path through a manifold. A second dialysate can be flowed in a regeneration circuit through the manifold and sorbent cartridge along a second flow path, and into a dialysate reservoir. The second dialysate can be flowed out of the dialysate reservoir along a third flow path through a first lumen of a dialyzer. The first dialysate can be flowed through a second lumen of the dialyzer, separated from the first lumen by at least one semipermeable membrane. The first dialysate can be flowed into a peritoneal cavity. The first dialysate can be maintained in the peritoneal cavity for a suitable dwell time, and then it can be flowed out of the peritoneal cavity.

The first and/or second dialysates can be heated in the dialysate reservoir. The first and second dialysates can be flowed using at least one pump. For example, the at least one pump can include at least one peristaltic pump, another pump described herein, or any other pump compatible with the methods and systems of the present invention. The first dialysate can be pumped along the first flow path using a first pump, the second dialysate can also be pumped along the second flow path using a second pump, and the second dialysate can be pumped along the third flow path using a third pump. Electrolytes can be pumped into the regeneration circuit using a fourth pump. The method can include measuring for the presence of air, and triggering an alarm or other warning if air is detected. The method can include measuring a pressure of the first dialysate in the peritoneum circuit. The flow of the first dialysate into and/or out of the peritoneal cavity can be adjusted to control the dialysate pressure to keep it below a pre-determined value. The amount of dialysate added to and/or removed from the peritoneum can be controlled using pressure transducers, in-line flow meters, non-evasive flow meters, or any combination thereof. The same or similar devices can be used for measurements. Examples of non-evasive flow meters include Transonic™ flow meters available from Transonic Systems, Inc., Ithaca, N.Y.

The first dialysate can be flowed through the dialysate circuit through the sorbent cartridge and the manifold along a fourth flow path, and across the at least one semipermeable membrane from the first lumen to the second lumen and into the peritoneum circuit. The fourth flow path can include at least one filter located between the manifold and the first lumen. The at least one filter can include a second dialyzer. The first, second, or any additional dialyzer can be chosen from any suitable dialyzer compatible with the methods, machines, and systems of the present invention. A polysulfone dialyzer can be used. For example, the dialyzer can be an F180PSD, an F180NRE, an Optiflux®, a Hemaflow™, or an Ultraflux dialyzer available from Fresenius Medical Care North America, Waltham, Mass. The dialyzers described in U.S. Pat. Nos. 4,141,836, 4,172,794, 4,261,830, 5,882,516, 6,802,821 B2, U.S. Pat. No. 6,911,007 B2, U.S. Pat. No. 8,202,428 B2, and U.S. Pat. No. 8,303,807 B2 can be used, all of which patents are incorporated herein by reference in their entireties. The dialyzers described in U.S. Patent Application Publications Nos. US 2005/0236330 A1, US 2009/007862 A1, US 2009/0223880 A1, US 2012/0172736 A1, and US 2013/0004593 A1 can be used, and all of these publications are incorporated herein by reference in their entireties. An ion-rejecting dialyzer membrane can be used, which can reduce or eliminate the need for added electrolytes and, accordingly, increase portability.

The second dialysate can be drained from the regeneration circuit along a fifth flow path. The first dialysate can be flowed across the semipermeable membrane along a sixth flow path from the second lumen to the first lumen, to transfer the first dialysate out of the peritoneum circuit and into the dialysate circuit. The weight of the first dialysate can then be measured. The weight of the first dialysate measured after flowing the first dialysate out of the peritoneum circuit and into dialysate circuit can be compared with an earlier measured weight of the first dialysate to determine at least one of ultrafiltration volume and ultrafiltration rate. The first dialysate can be flowed along a seventh flow path back across the semipermeable membrane from the first lumen to the second lumen, out of the regeneration circuit, and into the peritoneum circuit. The seventh flow path can contain at least one filter located between the manifold and the first lumen. The regeneration circuit can be filled with fresh dialysate to reform the second dialysate.

The manifold can be engaged with a dialysis machine configured to carry out the method. The manifold can be placed in fluid communication with a supply of dialysate. Any suitable manifold can be used in accordance with the present invention. A peritoneal dialysis system configured to perform the method is also provided in accordance with the present invention. The system can include one or more of a manifold, a dialysis machine in operable communication with the manifold and configured to pump the dialysate through the first, second, and third flow paths, a dialysate reservoir in fluid communication with the manifold, a filter in fluid communication with the manifold, a sorbent cartridge in fluid communication with the manifold, a scale configured to weigh the dialysate reservoir, and a heater configured to heat dialysate in the dialysate reservoir.

A sorbent cartridge for use in the present invention can contain one or more of activated carbon, urease, zirconium phosphate, zirconium carbonate, and zirconium oxide. Any suitable sorbent cartridge can be used. For example, a HISORB® or HISORB®+ sorbent cartridge available from Renal Solutions, Inc. of Warrendale, Pa. can be used. The sorbents and sorbent cartridges described in U.S. Pat. Nos. 3,989,622, 4,190,047, 4,213,859, 4,247,393, 4,661,246, 5,277,820, 5,536,412, 5,919,369, 5,944,684, 6,348,162 B1, U.S. Pat. No. 6,960,179 B2, U.S. Pat. No. 7,033,498 B2, U.S. Pat. No. 7,169,303 B2, U.S. Pat. No. 7,208,092 B2, U.S. Pat. No. 7,736,507 B2, U.S. Pat. No. 7,867,214 B2, U.S. Pat. No. 7,922,686 B2, U.S. Pat. No. 7,922,911 B2, B2, U.S. Pat. No. 8,080,161 B2, U.S. Pat. No. 8,096,969 B2, U.S. Pat. No. 8,105,487 B2, U.S. Pat. No. 8,187,250 B2, U.S. Pat. No. 8,220,643 B2, and U.S. Pat. No. 8,357,113 B2 can be used, and all of these patents are incorporated herein by reference in their entireties. Sorbents and sorbent cartridges described in U.S. Patent Application Publications Nos. US 2002/0112609 A1, US 20030097086 A1, US 20030114787 A1, US 2004/0019312 A1, US 2004/0019320 A1, US 2004/0050789 A1, US 2004/0082903 A1, US 2005/0006296 A1, US 2005/0131332 A1, US 2007/0158267 A1, US 2007/0179431 A1, US 2007/0213665 A1, US 2009/0120864 A1, US 2009/0127193 A1, US 2009/0264812 A1, US 2009/0314707 A1, US 2010/0010429 A1, US 2010/0010430 A1, US 2010/0078387 A1, US 2010/0100027 A1, US 2010/0114012 A1, US 2010/0217181 A1, US 2010/0230346 A1, US 2010/0312172 A1, US 2010/0312174 A1, US 2010/0314314 A1, US 2011/0017665 A1, US 2011/0155667 A1, US 2011/0171713 A1, US 2011/0184340 A1, US 2011/0272337 A1, US 20110297593 A1, US 2011/0303588 A1, US 2011/0303590 A1, US 20120248017 A1, US 2011/0315611 A1, US A1, US 2012/0271227 A1, or US 2013/0008852 A1 can be used, and all of these publications are incorporated herein by reference in their entireties. Dialysis regeneration can be achieved using other techniques instead of, or in addition to, sorbent-based techniques, to remove toxins or other species. For example, electrodialysis can be used as described in U.S. Patent Application Publications Nos. US 2012/0273354 A1 and US 2012/0220926 A1, which are incorporated herein by reference in their entireties.

The methods, manifolds, machines, and systems of the present invention can be used or modified for use in performing hemodialysis, hemofiltration, hemodiafiltration, peritoneal dialysis, or any combination thereof, while still falling within the scope of the present invention. For a peritoneal dialysis mode, the same manifold can be utilized that is used in a hemodialysis mode, with or without modification of tubing and/or other disposables attached to the manifold. A reservoir bag can be used in, or as, the dialysis reservoir. In addition to the reservoir bag, a drain bag can be used, for example, as the drain reservoir or part thereof. The drain bag can be placed within, alongside, or at a different location from the reservoir bag. Both the reservoir bag and the drain bag can be weighed on the same scale, or on separate scales, in order to determine the ultrafiltrate volume from a patient, prior to sending the contents to a drain. Peritoneal dialysate supplied from dialysate supply bags can be pumped into the reservoir using a pump segment used for pumping blood during hemodialysis. An appropriate fill volume of peritoneal dialysate can be weighed by the scale and heated by the heater. An air sensor can be used to help assure that air is not being introduced from the dialysate supply bags. Once warmed to an appropriate temperature, the dialysate can be pumped out of the reservoir bag, via a pump and bypass valve, and to the patient, via the manifold. Upon completion of the dwell cycle in the patient, dialysate fluid can be pumped from the patient back through the manifold, using a pump and a valve, and into the drain bag to be weighed. Upon recording the weight, the pump can be reversed and the dialysate can be pumped to the drain via the manifold.

Pressure sensors located at the outlet of the second dialysate pump and at the inlet of a pump can be used to help assure that maximum tolerable pressures within the peritoneum of the patient are not exceeded. Dialysate from a last bag can be pulled in, through the manifold, via two valves using the same pump or a different pump, and then heated in the reservoir bag. The reservoir bag can be emptied before pulling the dialysate from the last bag, by pumping out any remaining dialysate through valves, to minimize any mixing of dialysates.

The systems of the present invention can be used to regenerate peritoneal dialysate. A pump tube normally used for engaging a pump during hemodialysis need not be used and one end of a dialyzer can be closed off so that the dialysate infused into and out of a patient go through the dialyzer membrane to maintain the sterility of the dialysate. Peritoneal dialysate can be drawn into the system from supply bags, through the manifold, using a pump where a fill/drain line is located. The peritoneal dialysate can be pushed through a sorbent cartridge, where calcium, magnesium, and potassium can be removed. After exiting the sorbent cartridge, the peritoneal dialysate can enter the reservoir bag where it is weighed and warmed. To infuse a first fill into the patient, a pump can be used to draw the peritoneal dialysate out of the reservoir. The correct amount of electrolytes, for example, calcium, magnesium, and potassium, can be infused into the peritoneal dialysate using a pump to pull electrolytes from an electrolyte source. A pump can then pump the fortified peritoneal dialysate through valves in the manifold and across a dialyzer membrane or other filter. A suitable manifold valve can be closed at this time to assure that the peritoneal dialysate goes into the top of the dialyzer, to help maximize use of the full capacity of the membranes, and into the peritoneal cavity. Pressure sensors and air sensors in the line running from/to the patient can be activated along with the added safety of a pinch valve for possible failures. Upon completion of a dwell period, spent peritoneal dialysate can be pumped out of the cavity peritoneal using a pump. The spent peritoneal dialysate is then flowed across a semipermeable membrane, through the sorbent cartridge, and back into the reservoir bag for the next fill. Ultrafiltrate volume can be determined by how much fluid gets returned to the reservoir, which is weighed by a scale. Depending upon the sterility of the solution going to the patient, two dialyzers, and/or other filters, can be linked together. Instead of, or in addition to, the use of prepared (for example, bagged) peritoneal dialysate, tap water can be used for the initial solution that is run through the sorbent cartridge and subsequently fortified with electrolytes. A pump can be used to infuse glucose if needed. A last bag of peritoneal dialysate can be used.

The flow path of a peritoneal mode can be configured similar to the flow path of a hemodialysis mode. A secondary dialyzer can be utilized in the circuit for sterile protection. Water can be pulled up through a fill/drain valve and processed through a sorbent cartridge. The water can contain sodium in an amount that depends on how much urea is to be processed. The initial fluid can then be supplemented with the appropriate amount of electrolytes, for example, calcium, magnesium, and potassium. A fill volume can be infused into the patient's peritoneum by using appropriate valves and pumps and closing, stopping, or disabling others. Spent peritoneal dialysate can then be recirculated at a low flow rate via a pump through the primary dialyzer while other pumps circulate peritoneal dialysate through the secondary dialyzer and the primary dialyzer at a zero ultrafiltration rate. On the peritoneum side of the system, the patient connections can be connected to a dual lumen catheter for continuous recirculation through the peritoneum via a pump that would be akin to the blood pump during a hemodialysis mode. A pump that would be a heparin pump in a hemodialysis configuration can be used to replenish glucose levels in the dialysate on the peritoneum side of the system.

The ultrafiltrate volume can be determined using appropriate valves and pumps and closing, stopping, or disabling others to periodically empty the peritoneal dialysate from the peritoneum into a reservoir operatively associated with a scale. This procedure can be performed while monitoring the pressure sensors in the peritoneum circuit. The difference between the initially infused volume of peritoneal dialysate and the measured volume of peritoneal dialysate post-drain can be equated with the ultrafiltrate volume. A pump can subsequently be used to re-infuse the initial fill volume back into the peritoneum and the process of recirculation can continue.

The present invention can use manifolds, disposables, dialysis machines, dialysis systems, methods or any other aspect of dialysis as described in U.S. Patent Application Publications Nos. US 2012/0280154 A1, US 2012/0204968 A1, US 2012/0103885 A1, US 2012/0090706 A1, US 2012/0073365 A1, US 2011/0315611 A1, US 2011/0054378 A1, US 2010/0331754 A1, US 2010/0252490 A1, US 2010/234786 A1, US 2010/0184198 A1, US 2010/0179464 A1, US 2010/0140149 A1, US 2010/0116740 A1, US 2010/0116048 A1, US 2009/0173682 A1, US 2009/0114037 A1, US 2009/0101577 A1, US 2009/0101552 A1, US 2009/0076434 A1, which are all incorporated herein by reference in their entireties.

Figure 2:
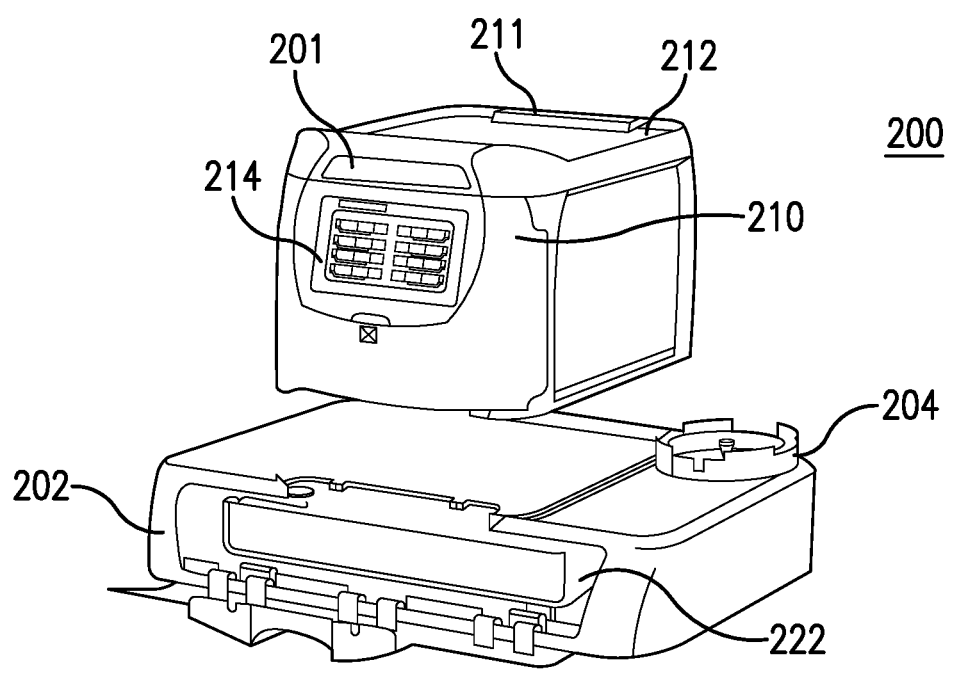
FIG. 2 is a right perspective view a dialysis system in accordance with the present invention, showing the modularity of the system.
Figure 3:
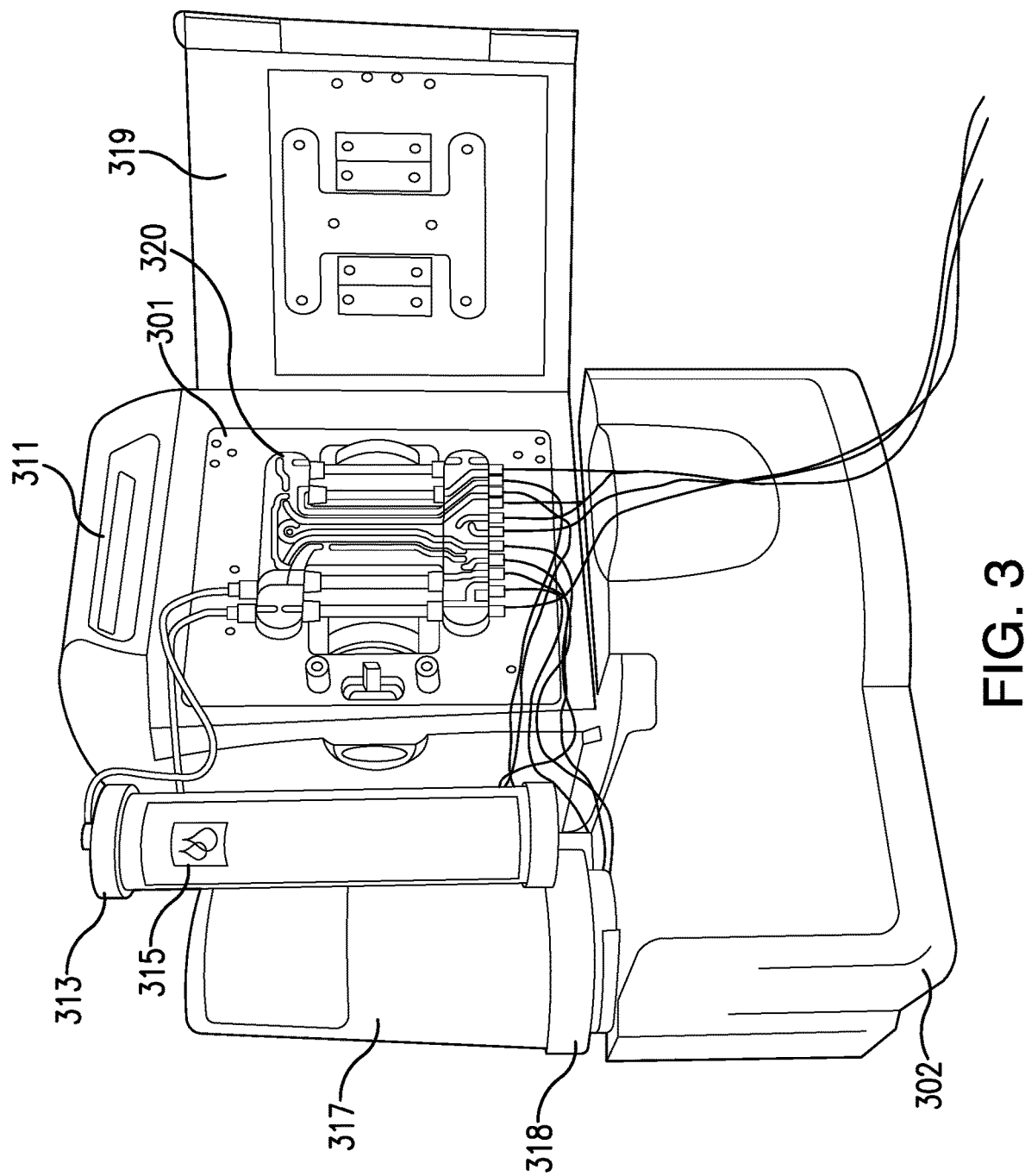
FIG. 3 is a left view of a dialysis system in accordance with the present invention, with the door open to show a manifold engaged with the system.

Referring to FIGS. 1, 2, and 3, the dialysis system 100, 200 includes a top unit 101, 201 that is detachably affixed to a base 102, 202. Base unit 102, 202 contains a reservoir 122, 222 for fluid storage, measurement, and monitoring. Top unit 101, 201, also referred to as the main unit or controller unit, includes a graphical user interface 114, 214, a pumping unit, and a door 110, 210 having a power lock. To a first side of top unit 101, 201, is a clasp 105 used to detachably affix a dialyzer 103, 313. Also to a side of top unit 101, 201, is a sorbent cartridge locking base 104, 204, 318, that is used to detachably affix a sorbent cartridge 107, 317. Clasp 105, hemofilter 103, 315, sorbent cartridge locking base 104, 204, 318 and sorbent cartridge 107, 317 can be positioned on the same side of top unit 101, as shown in FIG. 3, or on different sides or at different positions. In either case, base unit 102, 202, 302 can have a sufficiently larger top surface area relative to the top unit such that shelves can be formed on either side of the top unit to hold the sorbent cartridge, to hold an infusate jar, to capture any spillage, and/or to channel any leaks into a leak detector. With reference to FIG. 3, a door 319 is shown in an open position to reveal a manifold 320 mounted to the top unit 301. A handle 311 can be provided on top unit 301. The system configurations shown in FIGS. 1, 2, and 3 are exemplary and not limiting. For example, as shown in FIG. 3, top unit 301 can be positioned on one side of base unit 302, as opposed to being centrally positioned on top of base unit 302. Further details of suitable dialysis machines and components thereof, which can be used to carry out the methods of the present invention and form the systems of the present invention, are described, for example, in U.S. Patent Application Publication No. US 2011/0315611 A1, which is incorporated herein by reference in its entirety.

Figure 4:
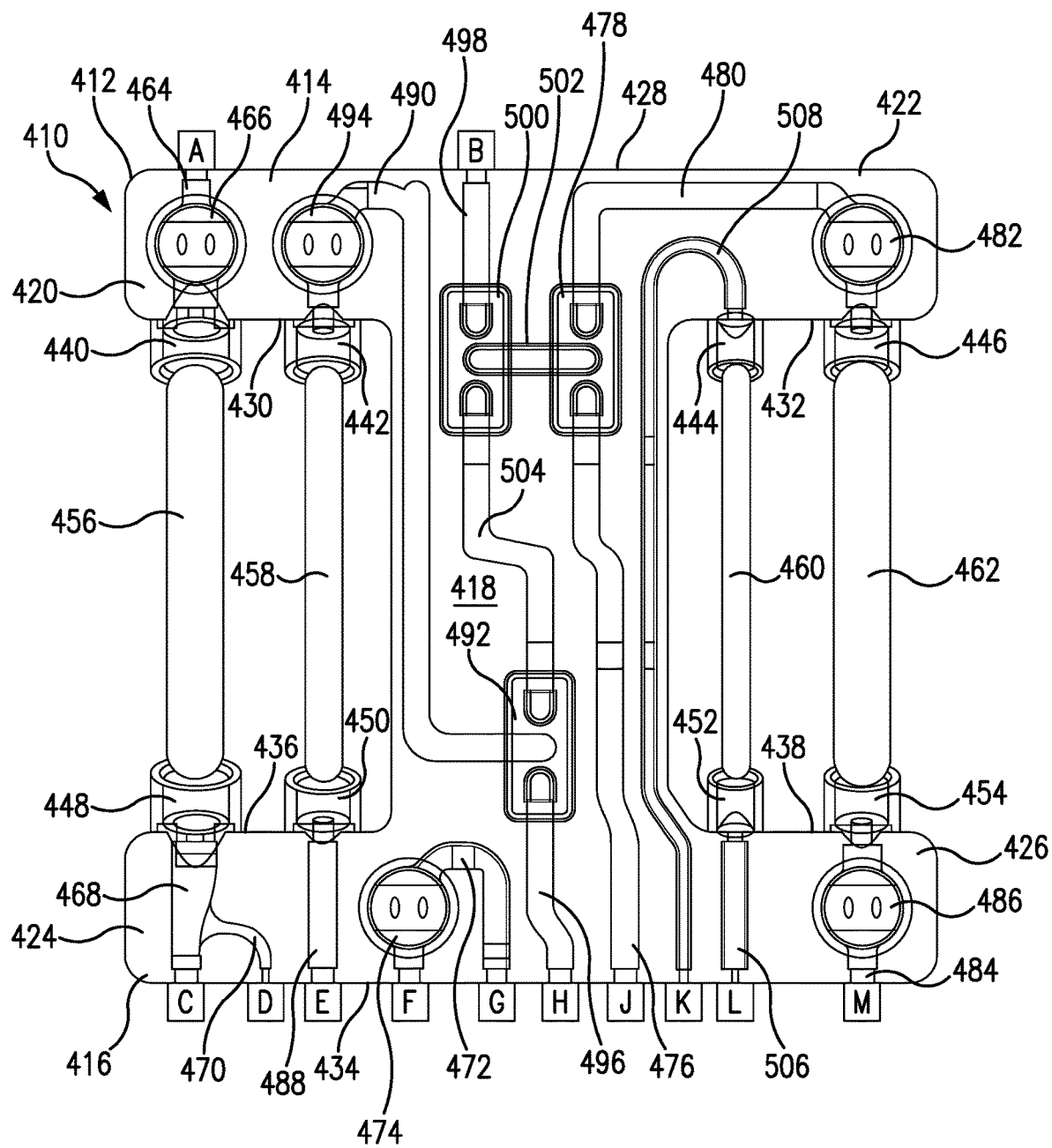
FIG. 4 is a front view of a manifold in accordance with the present invention.

With reference to FIG. 4, a manifold 410 can be provided that has a capital I-shaped body 412. Manifold body 412 can include a first transom 414 and a second transom 416 that are joined together by a central member or trunk 418. Both transoms can have first and second arms located on either side of trunk, for example, a first arm 420 can be on a left side of transom 414 and a second arm 422 can be on the right side of transom 414. Similarly, third and fourth arms 424, 426 can be on respective sides of second transom 416. First transom 414 can have first, second, and third edges 428, 430, and 432, respectively. First edge 428 spans first transom 414, and second edge 430 and third edge 432 are along first arm 420 and second arm 422, respectively. Second transom 416 can have fourth, fifth, and sixth edges, 434, 436, and 438, respectively. Fourth edge 434 spans second transom 416, and fifth edge 436 and sixth edge 438 are along third arm 424 and fourth arm 426, respectively.

Various conduits can be located in manifold body 412 and can be in fluid communication with valves, pressure sensor chambers, and other elements within manifold body 412 as well as being in fluid communication with one or more manifold ports on manifold body 412. The manifold ports can include intra-manifold ports and external ports. The intra-manifold ports can be joined by one or more pumping tube, and the external ports can fluidly connect the manifold to other portions of the dialysis machine and to the patient, via tubes. The tubes can be flexible. A flexible membrane or sheet can cover part of one or more sides of the manifold and can form part of the manifold body.

As depicted in FIG. 4, the external ports can be lettered from "A" to "M" (omitting "I"). The intra-manifold ports can be referred to by ordinal numbers, for example, 440, 442, 444, 446, 448, 450, 452, and 454. External ports A and B are shown along first edge 428 of first transom 414 and external ports C through M are arrayed along fourth edge 434 of second transom 416. First and second intra-manifold ports 440, 442 are arrayed along second edge 430 of first arm 420. Third and fourth intra-manifold ports 444, 446 are arrayed along third edge 432 of second arm 422. Fifth and sixth intra-manifold ports 448, 450 are arrayed along fifth edge 436 of third arm 424, and seventh and eighth intra-manifold ports 452, 454 are arrayed along sixth edge 438 of fourth arm 426. A first pumping tube 456 joins first and fifth intra-manifold ports 440, 448, respectively. A second pumping tube 458 joins second and sixth intra-manifold ports, 442, 450, respectively. A third pumping tube 460 joins third and seventh intra-manifold ports, 444, 452, fourth pumping tube 462 joins the fourth and eighth intra-manifold ports 446, 454, respectively.

A first conduit 464 can extend from external port A to first intra-manifold port 440 and can contain a first pressure sensor chamber 466. A second conduit 468 can extend from fifth intra-manifold port 448 to external port C. A third conduit 470 can branch off of second conduit 468 and extend to external port D. A fourth conduit 472 can extend between external port F and external port G, and can contain a second pressure sensor chamber 474. A fifth conduit 476 can extend from external port J to a first multivalve 478. A sixth conduit 480 can extend from first multivalve 478 to the fourth intra-manifold port 446, and can contain a third pressure sensor chamber 482. A seventh conduit 484 can extend from eighth intra-manifold port 454 to external port M, and can include a fourth pressure sensor chamber 486. An eighth conduit 488 can extend from external port E to sixth intra-manifold port 450. A ninth conduit 490 can extend from second intra-manifold port 442 to a second multivalve 492, and can include a fifth pressure sensor chamber 494. A tenth conduit 496 can extend from second multivalve 492 to external port H. An eleventh conduit 498 can extend from external port B to a third multivalve 500. A twelfth conduit 502 can connect third multivalve 500 to first multivalve 478, and a thirteenth conduit 504 can connect second and third multivalves 492, 500 respectively. A fourteenth conduit 506 can extend from external port L to seventh intra-manifold port 452. A fifteenth conduit 508 can extend from third intra-manifold port 444 to external port K. While certain conduits are described as containing a pressure sensor chamber, any conduit can contain any number of pressure sensor chambers. Each pressure sensor chamber can be independently covered by the flexible sheet and be aligned with a pressure sensor on a dialysis machine housing to allow for pressure measurements of a fluid with a given conduit. The multivalves can also be covered by the flexible sheet and can be aligned with actuators on a dialysis machine housing, the actuators being configured to control the multivalves and flow through the multivalves.

Figure 5:
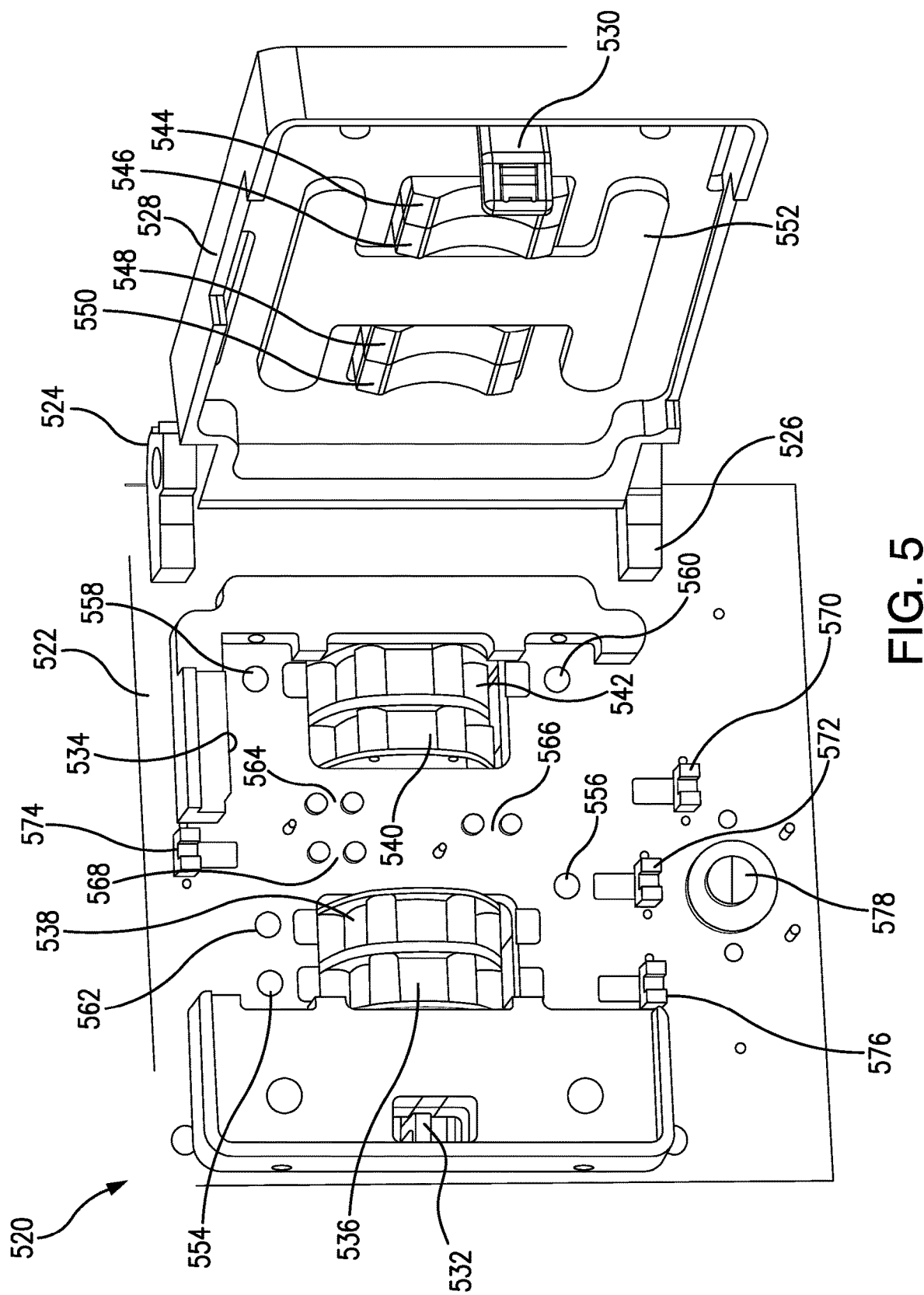
FIG. 5 is a left, perspective, close-up view of a dialysis system in accordance with the present invention, with the door open.

FIG. 5 is a partial view of a dialysis machine 520 in accordance with the present invention. Dialysis machine 520 has a machine housing 522 to which first and second hinges 524, 526, respectively, are mounted. A door 528 is, in turn, mounted to these hinges. Door 528 is shown in an open position in FIG. 5, but can be closed and secured with a door lock that includes a door lock insert 530 attached to door 528, and a door lock receptacle 532 disposed in machine housing 522. A manifold receptacle 534 is mounted on machine housing 522 and is configured to receive a manifold, for example, manifold 410 shown in FIG. 4. First, second, third, and fourth peristaltic pumps 536, 538, 540, and 542, respectively, are inset in machine housing 522 and positioned to engage first, second, third, and fourth pump tubes or pump headers, for example, pump tubes 456, 458, 460, and 462, shown in FIG. 4, respectively. First, second, third, and fourth pump shoes 544, 546, 548, and 550, respectively, are mounted on the inside of door 528 and are configured to press first, second, third, and fourth pump tubes of a manifold against first, second, third, and fourth peristaltic pumps 536, 538, 540, and 542, respectively. A platen 552 is also mounted on the inside of door 528 and is configured to press a manifold, for example, manifold 410, shown in FIG. 4, into manifold receptacle 534.

First, second, third, fourth, and fifth pressure sensors 554, 556, 558, 560, and 562, respectively, are positioned on machine housing 522 within manifold receptacle 534 to engage first, second, third, fourth, and fifth pressure sensor chambers 466, 474, 482, 486, and 494, shown in FIG. 4, respectively. A first set of valve actuators 564 is positioned in machine housing 522 within manifold receptacle 534, to engage first multivalve 478 shown in FIG. 4. A second set of valve actuators 566 is positioned in machine housing 522 within manifold receptacle 534 to engage second multivalve 492 shown in FIG. 4. A third set of valve actuators 568 is positioned in machine housing 522 within manifold receptacle 534 to engage third multivalve 500 shown in FIG. 4. First and second air detectors 570, 572 are included in machine housing 522. A blood leak detector 574, an occlusion detector 576, and a bloodline clamp 578, are also included in machine housing 522.

Figure 6:
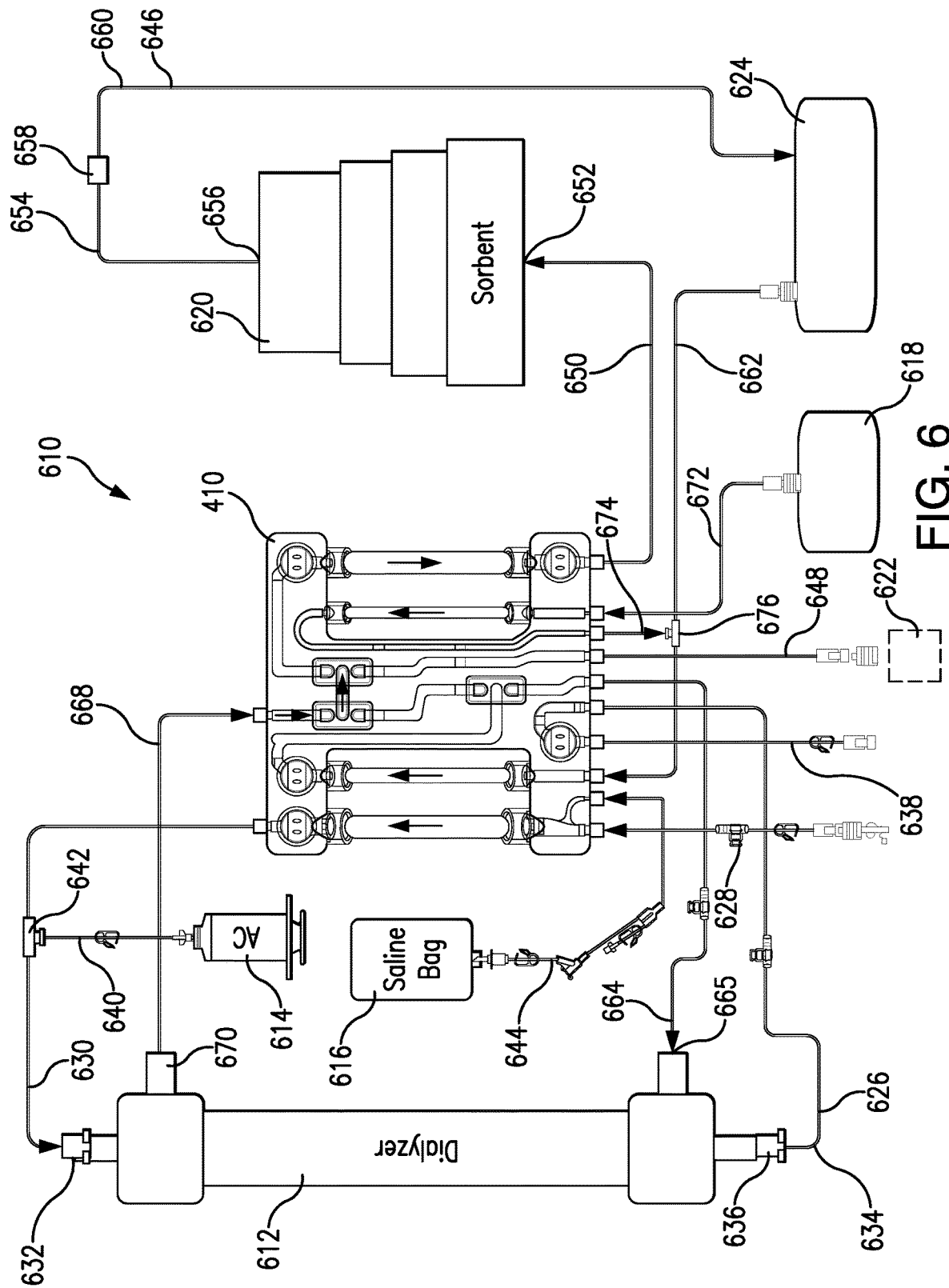
FIG. 6 is a schematic circuit diagram of a hemodialysis system in accordance with the present invention.

FIG. 6 shows a schematic diagram of a hemodialysis system 610 that can utilize a suitable manifold, for example, manifold 410, the details of which are shown in FIG. 4. External tubes, preferably flexible, are used to connect the manifold via the external ports to other components of the dialysis system, such as a dialyzer 612, an anticoagulant source 614, a saline source 616, an electrolyte source 618, a sorbent cartridge 620, a dialysate source 622, and a dialysate reservoir 624. Collectively, the manifold, external tubes, and other dialysis system components can form one or more circuits, for example, an extracorporeal blood circuit and a dialysate circuit. One can appreciate that a given tube can be made of one or more shorter tubes joined together by one or more connectors.

As can be seen in FIG. 6, an extracorporeal blood circuit 626 is provided in the hemodialysis system shown. A first external tube 628 can extend from the patient, for example, an artery of the patient, to external port C. A second external tube 630 can extend from external port A to a first dialyzer port 632. A third external tube 634 can extend from a second dialyzer port 636 to external port G. A fourth external tube 638 can extend from external port F back to the patient, for example, to a vein of the patient. A fifth external tube 640 can connect anti-coagulant source 614 to the extracorporeal blood circuit 626, for example, at a first branch point 642 in second external tube 630. A sixth external tube 644 can connect saline source 616 to external port D.

Figure 7:
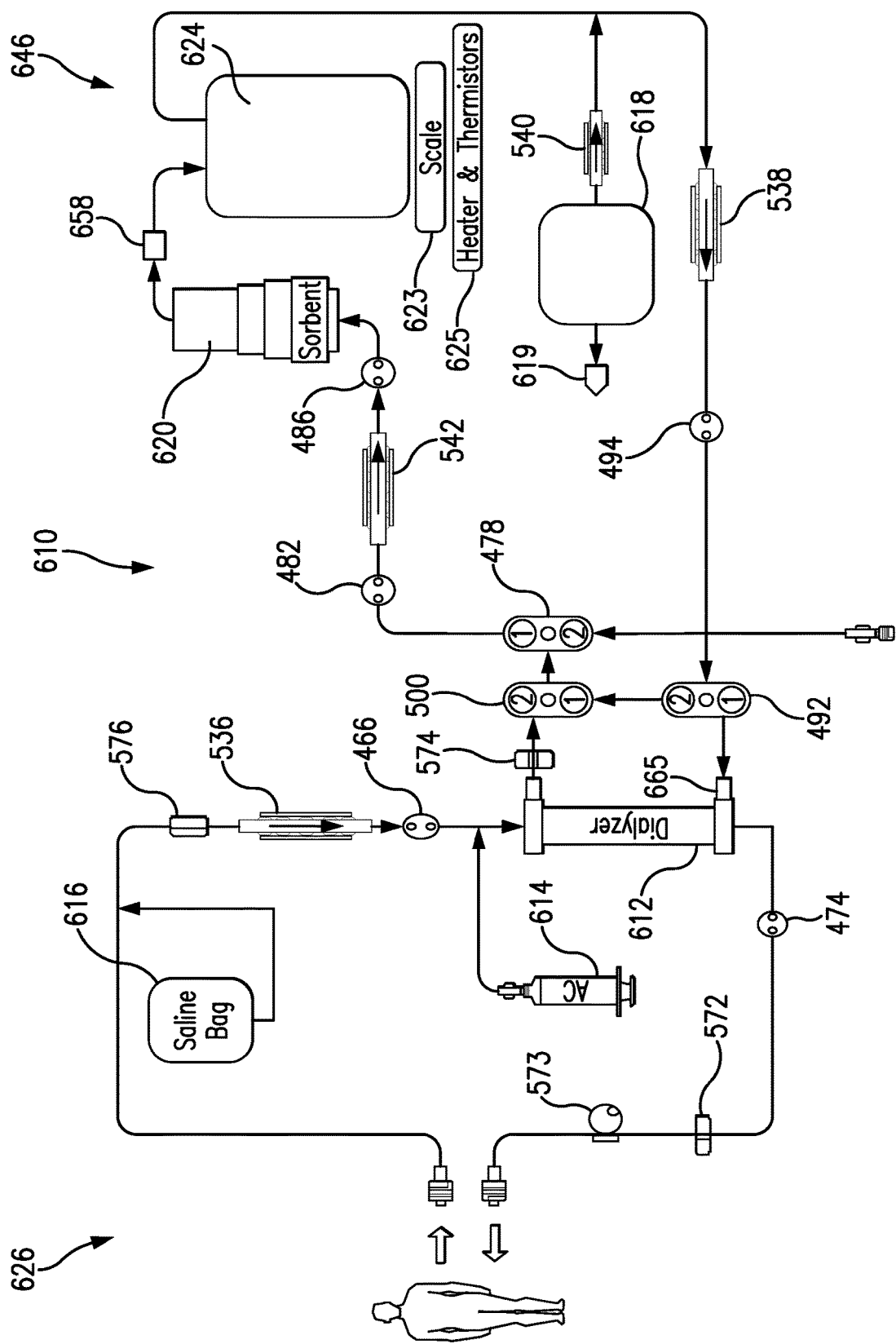
FIG. 7 is a schematic flow diagram corresponding to the schematic circuit diagram shown in FIG. 6.

With reference to FIGS. 4-6, blood can flow in extracorporeal blood circuit 626 in the following manner. The flow can be powered and controlled by first peristaltic pump 536, shown in FIG. 5, operatively associated with first pump tube 456, shown in FIG. 4. Blood can flow from the patient, for example, out of an artery, through first external tube 628, through second conduit 468, first pump tube 456, through first conduit 464, through second external tube 630, through dialyzer 612, through third external tube 634, through fourth conduit 472, through fourth external tube 638, and back to the patient, for example, into a vein of the patient. Anticoagulant can be supplied through fifth external tube 640 into extracorporeal blood circuit 626. A priming sequence can be used in extracorporeal blood circuit 626 by flowing saline from saline source 616 through external tube 644 and third conduit 470 into extracorporeal blood circuit 626, for example, at a location along second conduit 468. Flow in extracorporeal blood circuit 626 is also shown in FIG. 7, which further depicts a pinch valve 573.

A dialysate circuit 646 can also form part of hemodialysis system 610. A seventh external tube 648 can extend from a dialysate or water source 622 to external port J. An eighth external tube 650 can extend from external port M to a first sorbent cartridge port 652. A ninth external tube 654 can extend from a second sorbent cartridge port 656 to an ammonia sensor 658. A tenth external tube 660 can extend from ammonia sensor 658 to dialysate reservoir 624. An eleventh external tube 662 can extend from dialysate reservoir 624 to external port E. A twelfth external tube 664 can extend from external port H to a third dialyzer port 665. A thirteenth external tube 668 can extend from a fourth dialyzer port 670 to external port B. A fourteenth external tube 672 can extend from electrolyte source 618 to external valve port L. A fifteenth external tube 674 can extend from external port K to a second branch point 676 in eleventh external tube 662.

As can be seen in FIGS. 4-6, dialysate can flow through dialysate circuit 646, which can be powered by second and fourth peristaltic pumps 538, 542, respectively, shown in FIG. 5, which are in operative association with second and fourth pump tubes 458, 462, respectively, shown in FIG. 4. Third peristaltic pump 540 can be in operative association with third pump tube 460 to allow a flow of electrolytes to enter dialysate circuit 646. Dialysate, or water, can flow from dialysate source 622 through seventh external tube 648, fifth conduit 476, sixth conduit 480, fourth pump tube 462, seventh conduit 484, eighth external tube 650, sorbent cartridge 620, ninth external tube 654, ammonia sensor 658, tenth external tube 660, dialysate reservoir 624, eleventh external tube 662, eighth conduit 488, second pump tube 458, ninth conduit 490, tenth conduit 496, twelfth external tube 664, dialyzer 612, thirteenth external tube 668, eleventh conduit 498, twelfth conduit 502, and back to sixth conduit 480, to complete dialysate circuit 646. Electrolytes can flow through fourteenth external tube 672, fourteenth conduit 506, pump tube 460, fifteen conduit 508, and into dialysis circuit 646, for example, at second branch point 676 along eleventh external tube 662. Dialysate circuit 646 is also shown in FIG. 7, which further depicts a scale 623 and a heater/thermistor assembly 625, as well as a level detector 619 for measuring the amount of electrolyte solution in electrolyte source 618. In FIG. 7, the same reference numbers used in FIGS. 4-6 depict the same features.

Figure 8:
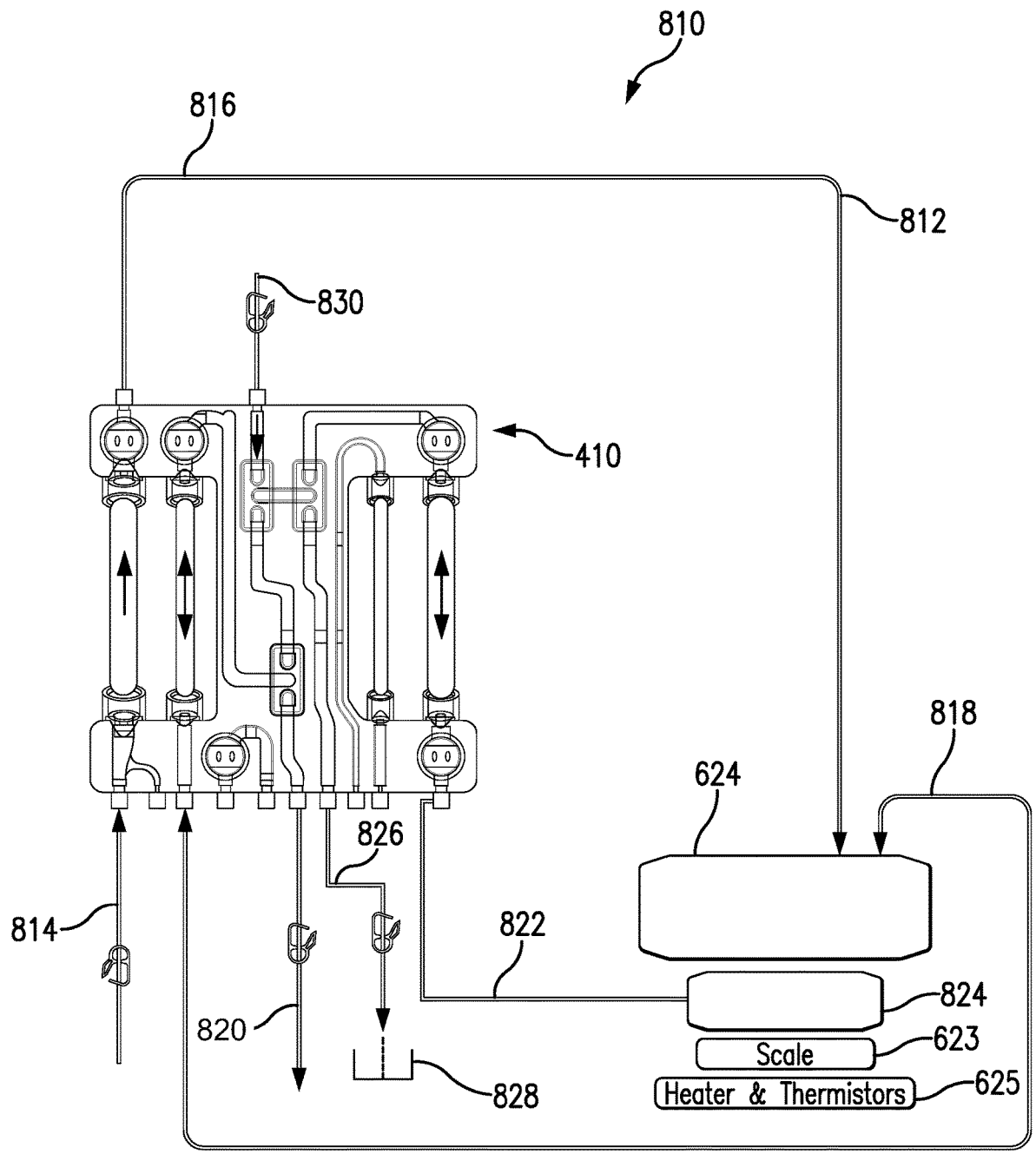
FIG. 8 is a schematic circuit diagram of a peritoneal dialysis system in accordance with the present invention.
Figure 9:
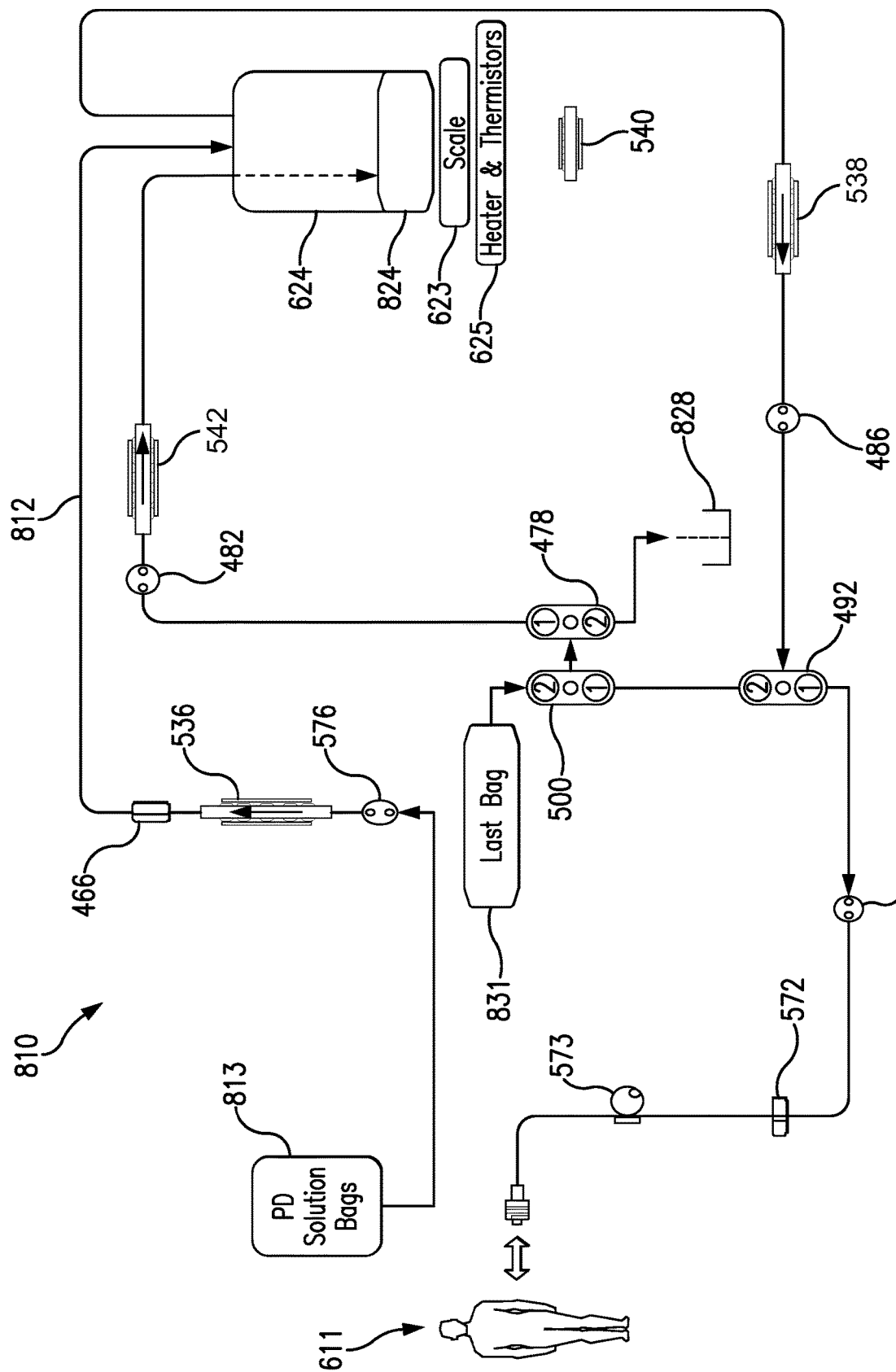
FIG. 9 is a schematic flow diagram corresponding to the schematic circuit diagram shown in FIG. 8.

FIG. 8 is a schematic circuit diagram of a peritoneal dialysis system 810 in accordance with the present invention. FIG. 9 is a schematic flow diagram of peritoneal dialysis system 810. Various components referred to in this description of peritoneal dialysis system 810 are shown in FIGS. 4-6 and discussed above, and the same reference numbers depict the same features. Dialysate can be pumped using first peristaltic pump 536 into a dialysate circuit 812 from an appropriate peritoneal dialysate source, for example, a prepared, sterile bag of dialysate 813, through a first external tube 814, external port C, second conduit 468, fifth intra-manifold port 448, first pump tube 456, first intra-manifold port 440, first conduit 464, external port A, a second external tube 816, and into dialysate reservoir 624. Dialysate can be heated and weighed in dialysate reservoir 624 and then pumped using second peristaltic pump 538 to the peritoneum of a patient through third external tube 818, external port E, eighth conduit 488, sixth intra-manifold port 450, second pump tube 458, second intra-manifold port 442, ninth conduit 490, second multivalve 492, tenth conduit 496, external port H, and fourth external tube 820. After a suitable dwell time, dialysate can be pumped back to dialysate circuit 812 using fourth peristaltic pump 542 through fourth external tube 820, external port H, tenth conduit 496, second multivalve 492, thirteenth conduit 504, third multivalve 500, twelfth conduit 502, first multivalve 478, sixth conduit 480, fourth intra-manifold port 446, fourth pump tube 462, eighth intra-manifold port 454, seventh conduit 484, external port M, fifth external tube 822, and into drain bag 824. The dialysate can be weighed in drain bag 824 before being pumped out and back to the manifold again using fourth dialysate pump 542, through fifth external tube 822, external port M, seventh conduit 484, eighth intra-manifold port 454, fourth pump tube 462, fourth intra-manifold port 446, sixth conduit 480, first multivalve 478, fifth conduit 476, external port J, sixth external tube 826, and into a waste receptacle 828. A "last bag" 831, for example, holding a dialysate having an alternative formulation to that used initially, can be pumped into dialysate circuit 812 using second dialysate pump 538, through a seventh external tube 830, external port B, eleventh conduit 498, third multivalve 500, thirteenth conduit 504, second multivalve 492, ninth conduit 490, second intra-manifold port 442, second pump tube 458, sixth intra-manifold port 450, eighth conduit 488, external port E, third external tube 818 and into dialysate reservoir 624. The dialysate can then be heated and weighed before being pumped to the peritoneal cavity, pumped back, and then drained in the manner described above for the original dialysate cycled through dialysate circuit 812.

Figure 10:
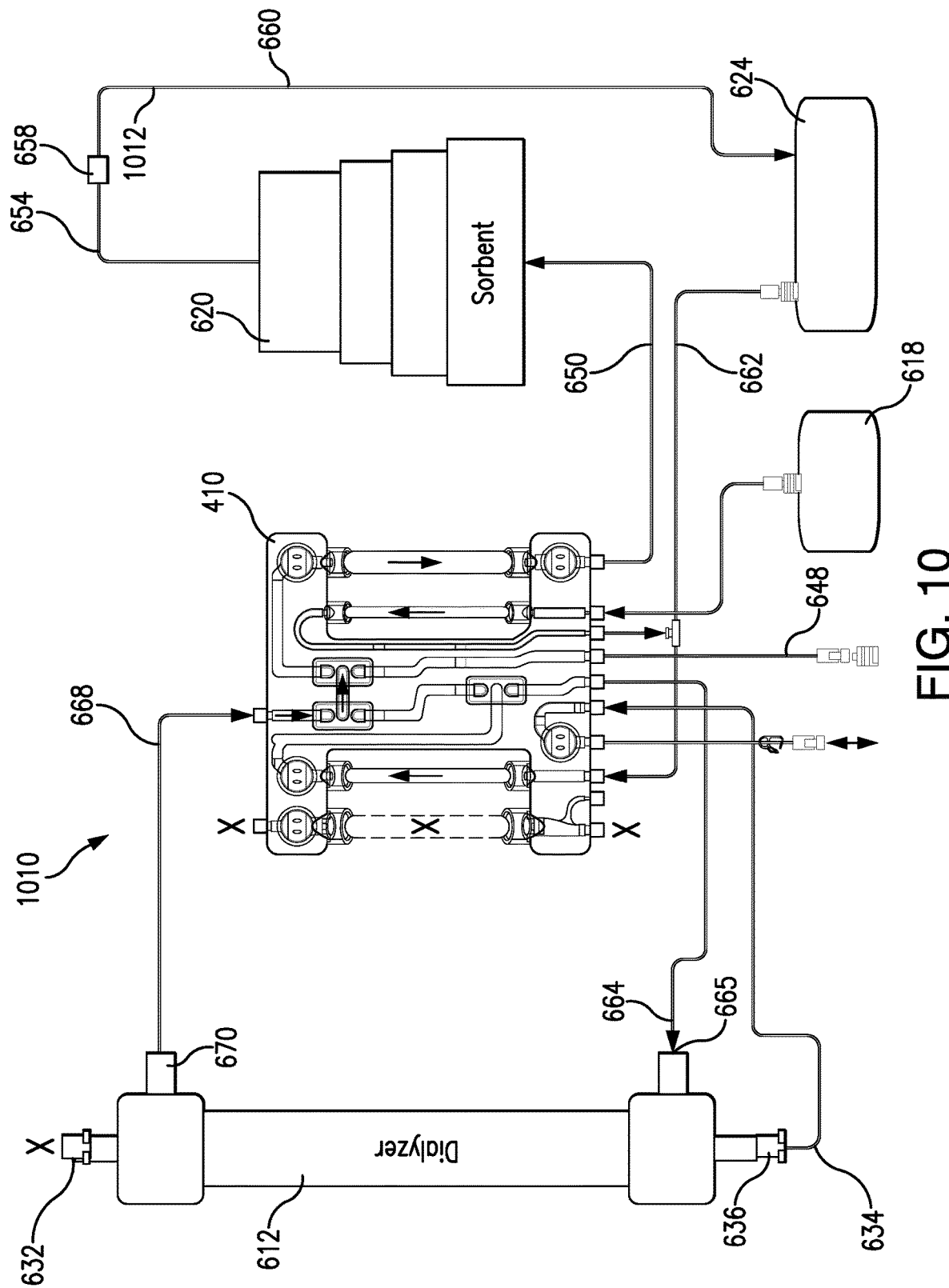
FIG. 10 is a schematic circuit diagram of a peritoneal dialysis system in accordance with the present invention.
Figure 11:
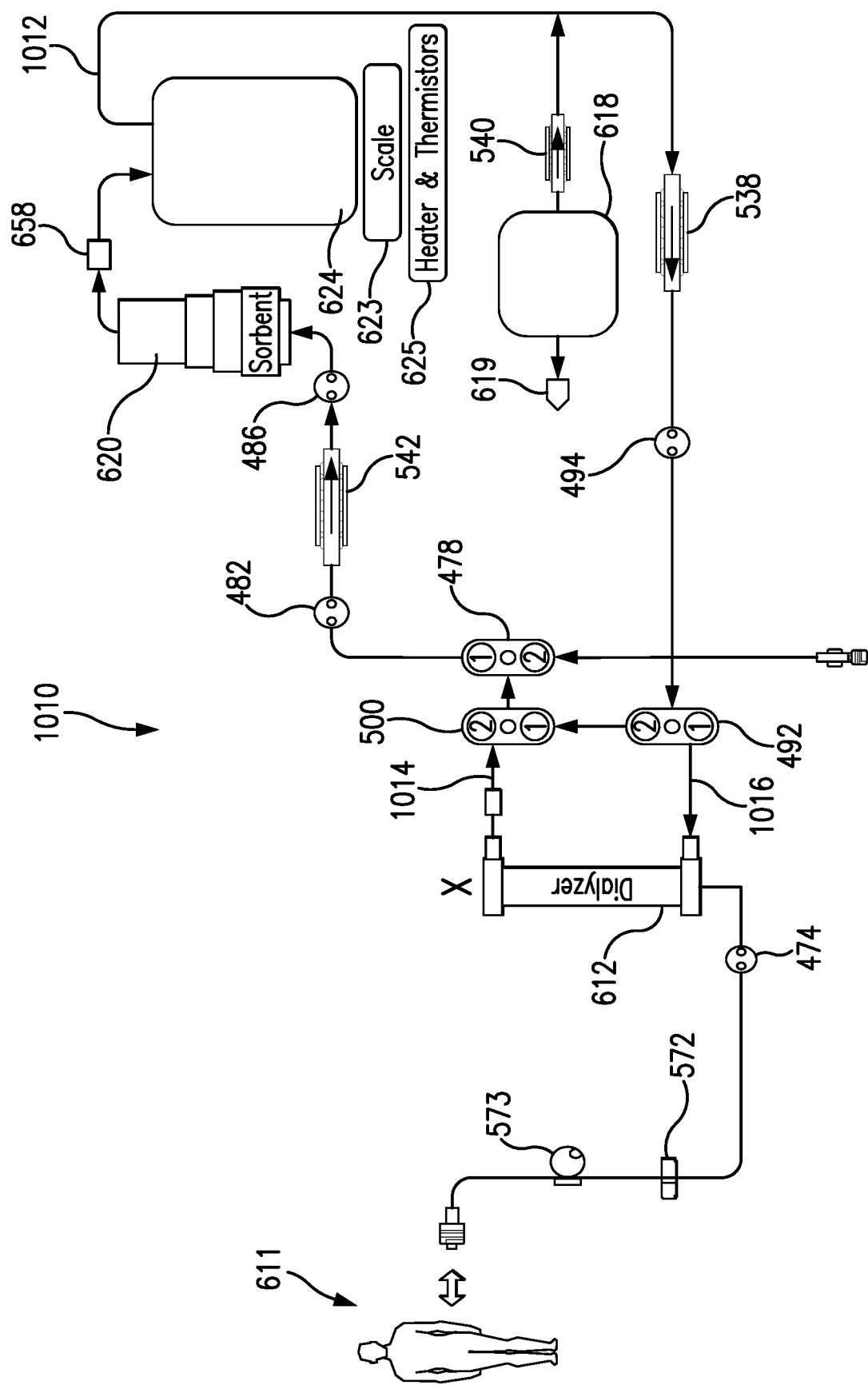
FIG. 11 is a schematic flow diagram corresponding to the schematic circuit diagram shown in FIG. 10.

FIG. 10 is a schematic circuit diagram of a peritoneal dialysis system 1010 in accordance with the present invention. FIG. 11 is a schematic flow diagram of peritoneal dialysis system 1010. Various components referred to in this description of peritoneal dialysis system 1010 are shown in FIGS. 4-6 and discussed above, and the same reference numbers depict the same features. Peritoneal dialysis system 1010 can be understood as a modification of hemodialysis system 610 shown in FIGS. 6 and 7, and uses manifold 410 shown in FIG. 4. The "X's" shown in FIGS. 10 and 11 show fluid paths from hemodialysis system 610, which are not utilized in system 1010. As peritoneal dialysis system 1010 is used for peritoneal dialysis with the peritoneum acting as the dialysis membrane, dialyzer 612 serves as a filter between the patient and dialysis circuit 1012. Dialysate, for example, prepared dialysate from an external source, can be pumped using fourth peristaltic pump 542 through seventh external tube 648, external port J, fifth conduit 476, first multivalve 478, sixth conduit 480, fourth intra-manifold port 446, fourth pump tube 462, eighth intra-manifold port 454, seventh conduit 484, eighth external tube 650, sorbent cartridge 620, ninth external tube 654, ammonia sensor 658, tenth external tube 660, and dialysate reservoir 624, then pumped using second peristaltic pump 538 through eleventh external tube 662, external port E, eighth conduit 488, sixth intra-manifold port 450, second pumping tube 458, second intra-manifold port 442, ninth conduit 490, and second multivalve 492, where the flow is split between first and second flow paths 1014, 1016, respectively. First flow path 1014 passes through eleventh conduit 498, external port B, thirteenth external tube 668, and into dialyzer 612 through fourth dialyzer port 670. The second flow path passes through tenth conduit 496, external port H, twelfth external tube 664, and into dialyzer 612 through third dialyzer port 665. First and second flow paths 1014, 1016 converge in dialyzer 612 and pass through the dialyzer, for example, semi-permeable membrane therein. The dialysate then passes through second dialyzer port 636, through third external tube 634, external port G, fourth conduit 472, external port F, and to the peritoneum of patient 611. After an appropriate dwell time, the dialysate is returned from patient 611 to dialysate circuit 1012. The process is reversed and first and second flow paths 1014, 1016 converge at third multivalve 500. The dialysate then flows through twelfth conduit 502, and back to sixth conduit 480 to complete dialysate circuit 1012. Electrolytes can be added to dialysate circuit 1012 from electrolyte source 618 using third peristaltic pump 540. Instead of splitting the dialysate flow, one of first and second flow paths 1014, 1016, respectively, can be used when pumping dialysate toward the peritoneum and the other of the two flow paths can be used when pumping dialysate from the peritoneum. In some cases, the same flow path can be used in both directions. Alternatively, dialysate flow can be split in one direction, and not split in the other direction. By maintaining different flow paths for the two directions, contamination between used and regenerated dialysate can be minimized or avoided.

Figure 12:
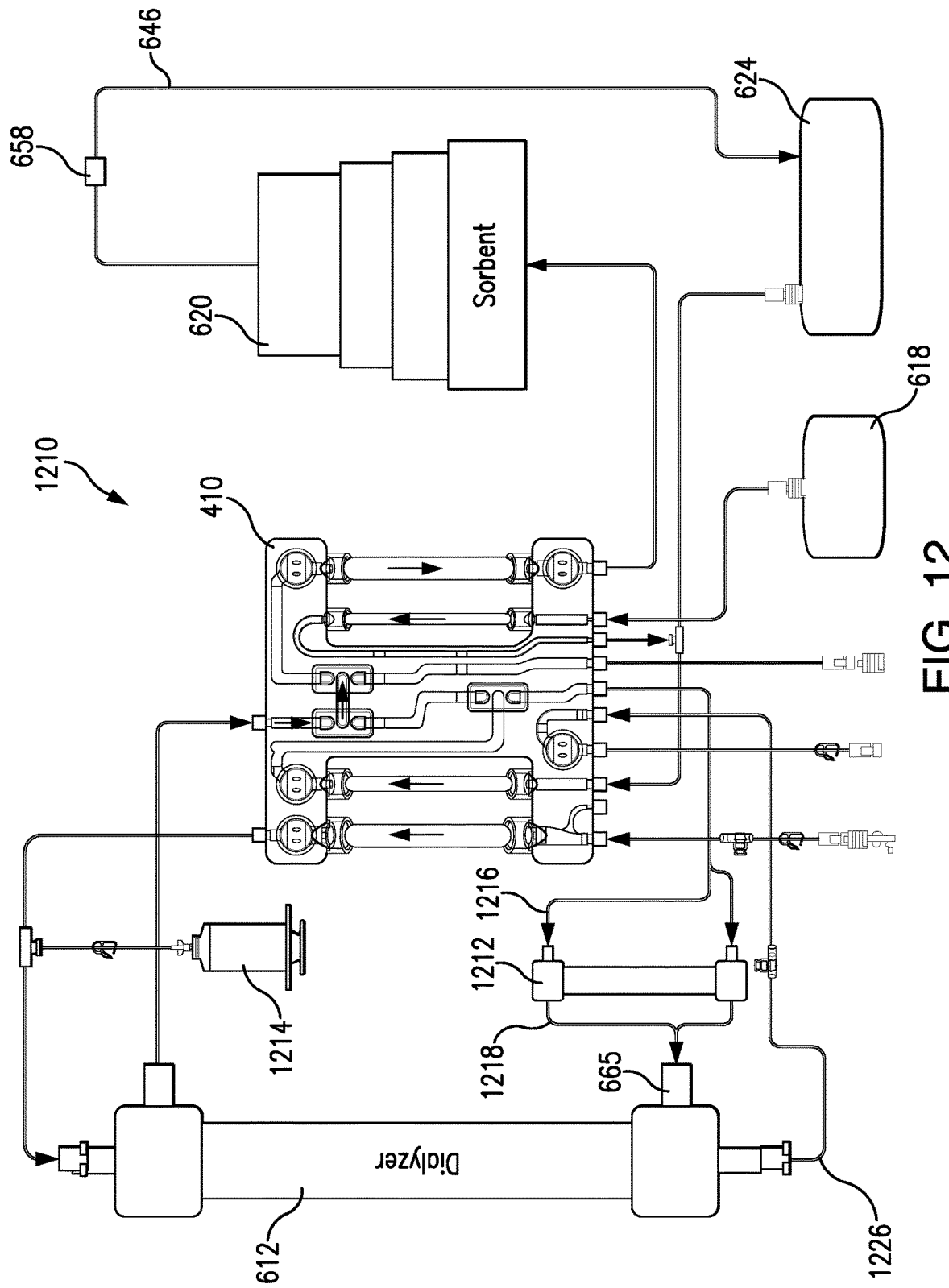
FIG. 12 is a schematic circuit diagram of a peritoneal dialysis system in accordance with the present invention.
Figure 13:
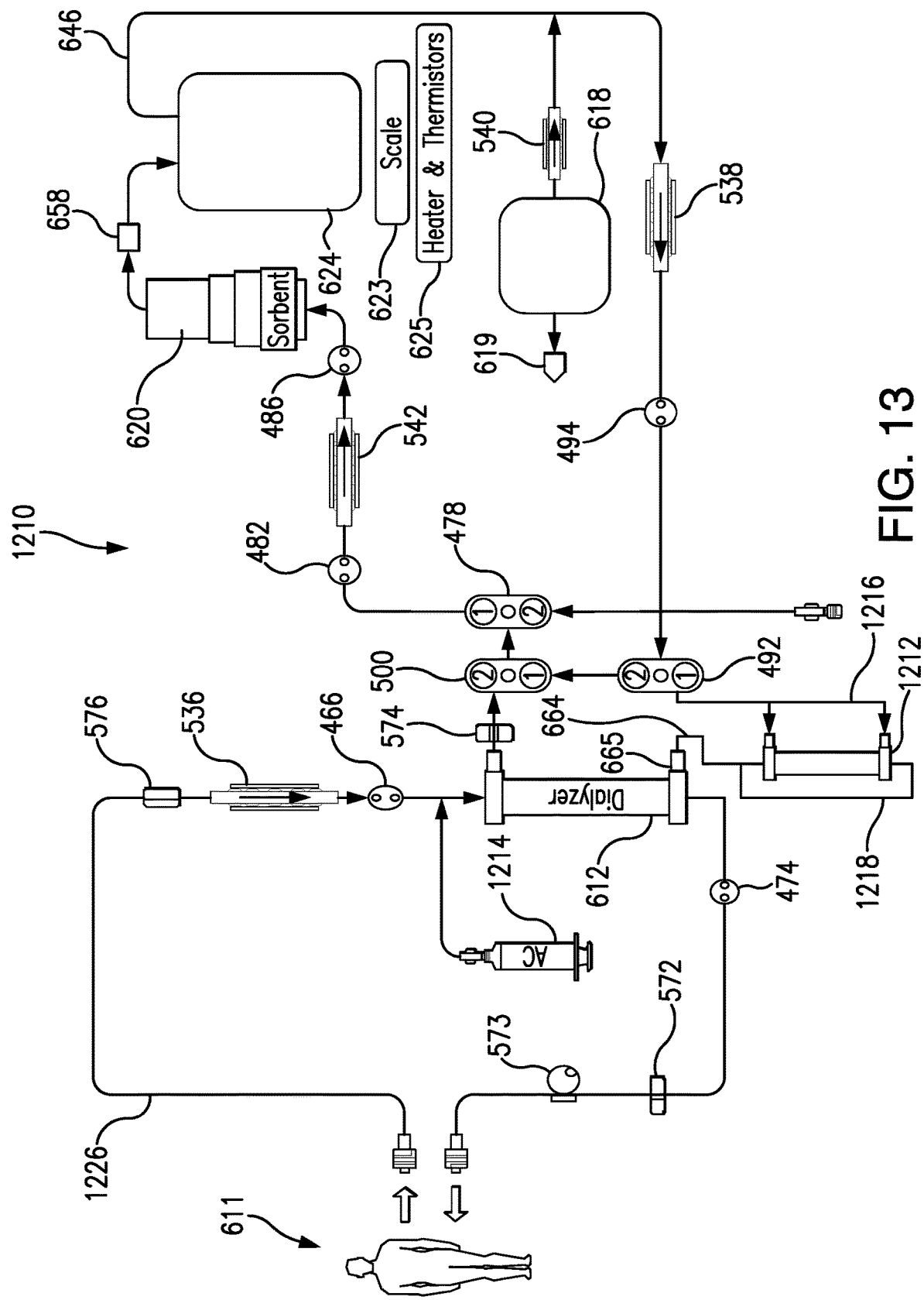
FIG. 13 is a schematic flow diagram corresponding to the schematic circuit diagram shown in FIG. 12.

FIG. 12 is a schematic circuit view of a peritoneal dialysis system 1210 in accordance with the present invention. FIG. 13 is a schematic flow diagram of peritoneal dialysis system 1210. Various components referred to in this description of peritoneal dialysis system 1210 are shown in FIGS. 4-6 and discussed above, and the same reference numbers depict the same features. Peritoneal dialysis system 1210 can be understood as a modification of hemodialysis system 610 shown in FIGS. 6 and 7, and uses manifold 410 shown in FIG. 4. In peritoneal dialysis system 1210, extracorporeal blood circuit 626 shown in FIGS. 6 and 7 becomes peritoneum circuit 1226. An anti-coagulant source is not needed as blood is not being circulated. Instead, a glucose source 1214, or other osmotic agent source, can take the place of anti-coagulant source 614. While the flow paths of hemodialysis system 610 can remain unchanged in peritoneal dialysis system 1210, various modifications can be made, for example, for sterility and anti-contamination purposes. For example, one or more bacterial filters can be placed in twelfth external tube 664. A second dialyzer 1212 can be used as such a filter. Twelfth external tube 664 can be replaced with a first branched tube 1216 and a second branched tube 1218. First branched tube 1216 can fluidly connect manifold 410 at external port H to second dialyzer 1212. Second branched tube 1218 can fluidly connect second dialyzer 1212 to third dialyzer port 665.

Dialysate for peritoneum circuit 1226 can be pumped in using first dialysate pump 536 from a prepared dialysate source through external port D and third conduit 470. Alternatively, or additionally, dialysate for peritoneum circuit 1226 can be prepared by pumping in dialysate and/or water from dialysate source 622 (FIG. 6) using fourth peristaltic pump 542 through seventh external tube 648, external port J, fifth conduit 476, sixth conduit 480, fourth pump tube 462, seventh conduit 484, eighth external tube 650, sorbent cartridge 620, ninth external tube 654, ammonia sensor 658, tenth external tube 660, and dialysate reservoir 624. Then, the dialysate can be pumped by second peristaltic pump 538 through eleventh external tube 662, eighth conduit 488, second pumping tube 458, ninth conduit 490, tenth conduit 496, and into dialyzer 612 through third and/or fourth dialyzer ports, 665, 670, respectively, wherein the dialysate passes through the membrane therein and into peritoneum circuit 1226. Dialysate can be similarly prepared for and retained in dialysate circuit 646. Continuous flow peritoneal dialysis can then be performed with a first dialysate flowing through peritoneum circuit 1226 to and from patient 611, and a second dialysate circulating through dialysate circuit 646 serving to dialyze the first dialysate across the membrane of dialyzer 612.

In peritoneal dialysis system 1210, the first dialysate can be periodically weighed by draining off the second dialysate from dialysate circuit 646 and flowing the first dialysate across the membrane of dialyzer 612 from peritoneum circuit 1226 into dialysate circuit 646. This transfer can be performed to determine ultrafiltration and can be achieved by stopping first and second peristaltic pumps 536, 538, respectively, while continuing to pump with fourth dialysate pump 542 to deliver the first dialysate to dialysate reservoir 624 to be weighed using scale 623. A difference between the initial weight of the first dialysate infused into peritoneum circuit 1226, and the resulting first dialysate, can be used as a determination of ultrafiltration. The first dialysate can then be pumped back into peritoneum circuit 1226, and dialysate circuit 646 can be refilled with dialysate to provide a second dialysate again. The dialysis process can then be restarted.

The present invention includes the following aspects/embodiments/features in any order and/or in any combination:

1. The present invention relates to a method of performing peritoneal dialysis comprising:

flowing dialysate along a first flow path through a manifold and into a dialysate reservoir;

weighing the dialysate in the dialysate reservoir to obtain a first weight;

flowing the dialysate out of the reservoir, along a second flow path through the manifold, and into a peritoneal cavity;

flowing the dialysate out of the peritoneal cavity, along a third flow path through the manifold, and into a drain reservoir;

weighing the dialysate in the drain reservoir to obtain a second weight; and flowing the dialysate out of the drain reservoir and along a fourth flow path through the manifold.

2. The method of any preceding or following embodiment/feature/aspect, further comprising heating the dialysate in the dialysate reservoir.

3. The method of any preceding or following embodiment/feature/aspect, wherein the dialysate reservoir and the drain reservoir are weighed using a common scale.

4. The method of any preceding or following embodiment/feature/aspect, further comprising determining the difference between the first weight and the second weight; and determining at least one of ultrafiltration volume and ultrafiltration rate based on the difference determined.

5. The method of any preceding or following embodiment/feature/aspect, wherein the manifold comprises at least four manifold conduits and each flow path comprises at least one manifold conduit that is fluidly isolated from the other three flow paths.

6. The method of any preceding or following embodiment/feature/aspect, wherein the manifold comprises at least two manifold conduits and at least two of the four flow paths comprise a common one of the at least two manifold conduits.

7. The method of any preceding or following embodiment/feature/aspect, wherein the dialysate is caused to flow by using at least one pump.

8. The method of any preceding or following embodiment/feature/aspect, wherein the at least one pump comprises at least one peristaltic pump.

9. The method of any preceding or following embodiment/feature/aspect, wherein the at least one pump comprises a first pump configured to control dialysate flow in one of the flow paths, and a second pump configured to control dialysate flow in a different one of the flow paths.

10. The method of any preceding or following embodiment/feature/aspect, wherein the at least one pump comprises a pump configured to control dialysate flow in more than one of the flow paths.

11. The method of any preceding or following embodiment/feature/aspect, further comprising detecting for the presence of air in one or more of the flow paths.

12. The method of any preceding or following embodiment/feature/aspect, further comprising measuring a pressure of the dialysate in at least one of the second and third flow paths.

13. The method of any preceding or following embodiment/feature/aspect, further comprising adjusting the flow of dialysate (1) into the peritoneal cavity, (2) out of the peritoneal cavity, or (3) both, to control the dialysate pressure and keep it below a pre-determined pressure.

14. The method of any preceding or following embodiment/feature/aspect, wherein, after flowing the dialysate through the fourth flow path the method is repeated starting with flowing a fresh supply of dialysate through the first flow path.

15. The method of any preceding or following embodiment/feature/aspect, further comprising flowing a fresh supply of dialysate through a fifth flow path in the manifold, and into the dialysate reservoir, after flowing the dialysate through the fourth flow path.

16. The method of any preceding or following embodiment/feature/aspect, wherein the fresh supply of dialysate differs in composition from the dialysate flow into the dialysate reservoir.

17. The method of any preceding or following embodiment/feature/aspect, further comprising engaging the manifold with a dialysis machine configured to carry out the method, forming a fluid communication between the manifold and a supply of dialysate.

18. The method of any preceding or following embodiment/feature/aspect, wherein the manifold comprises a first transom comprising a first edge, and second and third edges substantially parallel to the first edge, a trunk substantially perpendicular and adjacent to the first transom, and a second transom comprising a fourth edge, and fifth and sixth edges substantially parallel to the first, second, and third edges, wherein the second transom is substantially perpendicular and adjacent to the trunk and substantially parallel to the first transom.

19. A peritoneal dialysis system configured to perform the method of any preceding or following embodiment/feature/aspect, the system comprising:
the manifold;
a dialysis machine in operable communication with the manifold and configured to flow the dialysate through the first, second, third, and fourth flow paths.
the dialysate reservoir in fluid communication with the manifold;
the drain reservoir in fluid communication with the manifold;
a scale configured to weigh at least one of the dialysate reservoir and the drain reservoir; and
a heater configured to heat dialysate in the dialysate reservoir.

20. The method of any preceding or following embodiment/feature/aspect of performing peritoneal dialysis comprising:
flowing dialysate in a dialysate circuit through a first flow path, and into a dialysate reservoir, the first flow path comprising a flow path through a manifold and through a sorbent cartridge;
flowing the dialysate out of the dialysate reservoir and through the manifold along a second flow path that differs from the first flow path;
flowing the dialysate from the second flow path across at least one filter and into a peritoneum circuit;
flowing the dialysate through the peritoneum circuit and into a peritoneal cavity;
maintaining the dialysate in the peritoneal cavity;
flowing the dialysate out of the peritoneal cavity, through the peritoneum circuit, across the filter and back into the dialysate circuit; and
flowing the dialysate through the manifold along a third flow path and back into the dialysate reservoir, the third flow path comprising a flow path through the sorbent cartridge.

21. The method of any preceding or following embodiment/feature/aspect, further comprising heating the dialysate in the dialysate reservoir.

22. The method of any preceding or following embodiment/feature/aspect, further comprising weighing the dialysate in the dialysate reservoir (1) before the dialysate is flowed to the peritoneum to obtain a first weight (2) after the dialysate is returned to the dialysate reservoir to obtain a second weight, or (3) both.

23. The method of any preceding or following embodiment/feature/aspect, wherein the weighing comprises (3), and the method further comprises determining at least one of ultrafiltration volume and ultrafiltration rate based on a difference between the second weight and the first weight.

24. The method of any preceding or following embodiment/feature/aspect, wherein the manifold comprises at least three manifold conduits, and each flow path comprises at least one manifold conduit that is fluidly isolated from the other three flow paths.

25. The method of any preceding or following embodiment/feature/aspect, wherein the manifold comprises at least two manifold conduits and at least two of the three flow paths comprises a common one of the manifold conduits.

26. The method of any preceding or following embodiment/feature/aspect, wherein the third flow path comprises at least one conduit that is common to both the first and second flow paths, and the first and second flow paths comprise no conduit in common.

27. The method of any preceding or following embodiment/feature/aspect, wherein the dialysate is flowed using at least one peristaltic pump.

28. The method of any preceding or following embodiment/feature/aspect, wherein the at least one pump comprises a pump configured to control dialysate flow in more than one of the flow paths.

29. The method of any preceding or following embodiment/feature/aspect, further comprising detecting the presence of air in at least one of the flow paths.

30. The method of any preceding or following embodiment/feature/aspect, further comprising measuring a pressure of the dialysate in at least one of the second and third flow paths.

31. The method of any preceding or following embodiment/feature/aspect, further comprising adjusting the flow of dialysate (1) into the peritoneal cavity, (2) out of the peritoneal cavity, or (3) both, to control the dialysate pressure and keep it below a pre-determined pressure.

32. The method of any preceding or following embodiment/feature/aspect, wherein, after returning the dialysate through the third flow path to the dialysate reservoir, the method is repeated by flowing dialysate from the dialysate reservoir through the second flow path.

33. The method of any preceding or following embodiment/feature/aspect, wherein the at least one filter comprises at least one dialyzer.

34. The method of any preceding or following embodiment/feature/aspect, further comprising splitting the flow of dialysate in the second flow path between at least two different branch lines before passing across the flow in both branch lines the at least one filter.

35. The method of any preceding or following embodiment/feature/aspect, further comprising engaging the manifold with a dialysis machine configured to carry out the method, and forming a fluid communication between the manifold and a supply of dialysate.

36. The method of any preceding or following embodiment/feature/aspect, wherein the manifold comprises a first transom comprising a first edge, and second and third edges substantially parallel to the first edge,
a trunk substantially perpendicular and adjacent to the first transom, and
a second transom comprising a fourth edge, and fifth and sixth edges substantially parallel to the first, second, and third edges, wherein the second transom is substantially perpendicular and adjacent to the trunk and substantially parallel to the first transom.

37. A peritoneal dialysis system configured to perform the method of any preceding or following embodiment/feature/aspect, the system comprising:
the manifold;
a dialysis machine in operable communication with the manifold and configured to pump the first dialysate through the first flow path and configured to pump the second dialysate through the second and third flow paths;
the dialysate reservoir in fluid communication with the manifold;
the filter in fluid communication with the manifold;
the sorbent cartridge in fluid communication with the manifold;
a scale configured to weigh the dialysate reservoir; and
a heater configured to heat dialysate in the dialysate reservoir.

38. The method of any preceding or following embodiment/feature/aspect of performing peritoneal dialysis, comprising:
flowing a first dialysate in a peritoneum circuit along a first flow path, the first flow path comprising a flow path through a manifold;
flowing a second dialysate in a regeneration circuit along a second flow path and into a dialysate reservoir, the second flow path comprising a flow path through the manifold and through a sorbent cartridge;
flowing the second dialysate out of the dialysate reservoir along a third flow path through a first lumen of a dialyzer;
flowing the first dialysate through a second lumen of the dialyzer that is separated from the first lumen by at least one semipermeable membrane;
flowing the first dialysate into a peritoneal cavity;
maintaining the first dialysate in the peritoneal cavity, to form a dialysate; and
flowing the dialysate out of the peritoneal cavity.

39. The method of any preceding or following embodiment/feature/aspect, further comprising heating the second dialysate in the dialysate reservoir.

40. The method of any preceding or following embodiment/feature/aspect, wherein the first and second dialysates are flowed using at least one peristaltic pump.

41. The method of any preceding or following embodiment/feature/aspect, wherein the first dialysate is pumped along the first flow path using a first pump, the second dialysate is pumped along the second flow path using a second pump, and the second dialysate is pumped along the third flow path using a third pump.

42. The method of any preceding or following embodiment/feature/aspect, further comprising pumping electrolytes into the regeneration circuit using a fourth pump.

43. The method of any preceding or following embodiment/feature/aspect, further comprising detecting the presence of air in at least one of the flow paths.

44. The method of any preceding or following embodiment/feature/aspect, further comprising measuring a pressure of the first dialysate in the peritoneum circuit.

45. The method of any preceding or following embodiment/feature/aspect, further comprising adjusting the flow of the first dialysate (1) into the peritoneal cavity, (2) out of the peritoneal cavity, or (3) both, to control the dialysate pressure and keep it below a pre-determined pressure.

46. The method of any preceding or following embodiment/feature/aspect, further comprising flowing the first dialysate through the dialysate circuit along a fourth flow path, and across the at least one semipermeable membrane from the first lumen to the second lumen, and into the peritoneum circuit, wherein the fourth flow path comprises a flow path through the sorbent cartridge and the manifold.

47. The method of any preceding or following embodiment/feature/aspect, wherein the fourth flow path comprises at least one filter located between the manifold and the first lumen.

48. The method of any preceding or following embodiment/feature/aspect, wherein the at least one filter comprises a second dialyzer.

49. The method of any preceding or following embodiment/feature/aspect, further comprising:
draining the second dialysate from the regeneration circuit along a fifth flow path;
flowing the first dialysate across the semipermeable membrane from the second lumen to the first lumen to transfer the first dialysate out of the peritoneum circuit and into the dialysate circuit along a sixth flow path; and measuring the weight of the first dialysate.

50. The method of any preceding or following embodiment/feature/aspect, further comprising comparing the first dialysate weight measured after flowing the first dialysate out of the peritoneum circuit and into dialysate circuit, with an earlier measured weight of the first dialysate, to determine at least one of an ultrafiltration volume and an ultrafiltration rate.

51. The method of any preceding or following embodiment/feature/aspect, further comprising flowing the first dialysate along a seventh flow path back across the semipermeable membrane from the first lumen to the second lumen, out of the regeneration circuit, and into the peritoneum circuit.

52. The method of any preceding or following embodiment/feature/aspect, wherein the seventh flow path comprises a flow path through at least one filter located between the manifold and the first lumen.

53. The method of any preceding or following embodiment/feature/aspect, further comprising filling the regeneration circuit with dialysate to reform the second dialysate.

54. The method of any preceding or following embodiment/feature/aspect, further comprising engaging the manifold with a dialysis machine configured to carry out the method.

55. The method of any preceding or following embodiment/feature/aspect, wherein the manifold comprises:

a first transom comprising a first edge, and second and third edges substantially parallel to the first edge, a trunk substantially perpendicular and adjacent to the first transom, and a second transom comprising a fourth edge, and fifth and sixth edges substantially parallel to the first, second, and third edges, wherein the second transom is substantially perpendicular and adjacent to the trunk and substantially parallel to the first transom.

56. A peritoneal dialysis system configured to perform the method of any preceding or following embodiment/feature/aspect, the system comprising:

the manifold;

a dialysis machine in operable communication with the manifold and configured to pump the first dialysate through the first flow path, and configured to pump the second dialysate through the second and third flow paths, the dialysate reservoir in fluid communication with the manifold;

the filter in fluid communication with the manifold;

the sorbent cartridge in fluid communication with the manifold;

a scale configured to weigh the dialysate reservoir; and a heater configured to heat dialysate in the dialysate reservoir.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of performing peritoneal dialysis, the method comprising:

flowing dialysate in a dialysate circuit through a first flow path, and into a dialysate reservoir, the first flow path comprising a flow path through a manifold, out of the manifold, and through a sorbent cartridge, wherein the manifold comprises a body, internal passageways integrated into the body, a plurality of external ports on the body to allow for fluid communication with conduits or fluid passageways that are external to the body, a plurality of pairs of intra-manifold ports, and a plurality of pump tubes, each pair of the plurality of pairs of intra-manifold ports comprising a first intra-manifold port and a second intra-manifold port that are in fluid communication with one another through a respective one of the pump tubes;

flowing the dialysate out of the dialysate reservoir, back through the manifold along a second flow path that differs from the first flow path, and to a filter;

flowing the dialysate from the second flow path across the filter and into a peritoneum circuit, the filter and peritoneum circuit being in fluid communication with each other via a tube connecting the peritoneum circuit to a first outlet of the filter;

flowing the dialysate through the peritoneum circuit and into a peritoneal cavity;

maintaining the dialysate in the peritoneal cavity for a dwell time, to form spent peritoneal dialysate;

flowing, via a third flow path, the spent peritoneal dialysate out of the peritoneal cavity, through the peritoneum circuit, into the filter, out of the filter through a second outlet of the filter, through the manifold and into the dialysate circuit, the third flow path connecting the peritoneal cavity, the filter via the first and second outlets, the manifold, and the dialysate circuit, in fluid communication with each other; and further flowing the spent peritoneal dialysate through the third flow path and through the sorbent cartridge to form regenerated dialysate.

2. The method of claim 1, further comprising heating the dialysate in the dialysate reservoir.

3. The method of claim 1, further comprising: weighing the dialysate in the dialysate reservoir before the dialysate is flowed into the peritoneum circuit, to obtain a first weight; or weighing the dialysate in the dialysate reservoir after the dialysate is returned to the dialysate reservoir, to obtain a second weight; or weighing the dialysate in the dialysate reservoir before the dialysate is flowed into the peritoneum circuit, to obtain a first weight, and weighing the dialysate in the dialysate reservoir after the dialysate is returned to the dialysate reservoir, to obtain a second weight.

4. The method of claim 1, wherein the method further comprises weighing the dialysate in the dialysate reservoir before the dialysate is flowed into the peritoneum circuit, to obtain a first weight, weighing the dialysate in the dialysate reservoir after the dialysate is returned to the dialysate reservoir, to obtain a second weight, and determining at least one of an ultrafiltration volume and an ultrafiltration rate based on a difference between the second weight and the first weight.

5. The method of claim 1, wherein the manifold comprises at least three manifold conduits, and each flow path comprises at least one manifold conduit that is fluidly isolated from the other three flow paths.

6. The method of claim 1, wherein the manifold comprises at least two manifold conduits and at least two of the three flow paths comprise a common one of the manifold conduits.

7. The method of claim 6, wherein the third flow path comprises at least one conduit that is common to both the first and second flow paths, and the first and second flow paths comprise no conduit in common.

8. The method of claim 1, wherein the dialysate is flowed using at least one peristaltic pump.

9. The method of claim 8, wherein the at least one peristaltic pump comprises a pump configured to control dialysate flow in more than one of the flow paths.

10. The method of claim 1, further comprising detecting the presence of air in at least one of the flow paths.

11. The method of claim 1, further comprising measuring a pressure of the dialysate in at least one of the second and third flow paths.

12. The method of claim 11, further comprising adjusting the flow of dialysate (1) into the peritoneal cavity, (2) out of the peritoneal cavity, or (3) both, to control the dialysate pressure and keep it below a pre-determined pressure.

13. The method of claim 1, wherein, after returning the dialysate through the third flow path to the dialysate reservoir, the method is repeated by flowing dialysate from the dialysate reservoir through the second flow path.

14. The method of claim 1, wherein the at least one filter comprises at least one dialyzer.

15. The method of claim 1, further comprising splitting the flow of dialysate in the second flow path between at least two different branch lines before passing the flow in both branch lines across the at least one filter.

16. The method of claim 1, further comprising engaging the manifold with a dialysis machine configured to carry out the method, and forming a fluid communication between the manifold and a supply of dialysate.

17. The method of claim 1, wherein the manifold comprises
a first transom comprising a first edge, and second and third edges substantially parallel to the first edge,
a trunk substantially perpendicular and adjacent to the first transom, and
a second transom comprising a fourth edge, and fifth and sixth edges substantially parallel to the first, second, and third edges, wherein the second transom is substantially perpendicular and adjacent to the trunk and substantially parallel to the first transom.

18. A dialysis system configured to perform a peritoneal dialysis in a first mode and a hemodialysis in a second mode, the system comprising:
a manifold comprising a body, internal passageways integrated into the body, a plurality of external ports on the body to allow for fluid communication with conduits or fluid passageways that are external to the body, a plurality of pairs of intra-manifold ports, and a plurality of pump tubes, each pair of the plurality of pairs of intra-manifold ports comprising a first intra-manifold port and a second intra-manifold port that are in fluid communication with one another through a respective one of the pump tubes;
a first pump, a second pump, a third pump, and a fourth pump;
a dialysis machine in operable communication with the manifold and configured to operate at least three of the first pump, the second pump, the third pump, and the fourth pump when in the first mode and when in the second mode, wherein, during the second mode, the first pump is configured to pump blood from a hemodialysis patient, through the manifold, and back to the hemodialysis patient, the second pump and the fourth pump are configured to pump hemodialysis dialysate to and from a dialysate reservoir, and the third pump is configured to pump electrolyte into a hemodialysis dialysate circuit, and, during the first mode, the first pump is configured to pump peritoneal dialysate from a peritoneal dialysate source into a peritoneal dialysate circuit, the second pump is configured to pump peritoneal dialysate from the dialysate reservoir into a peritoneum of a peritoneal dialysis patient, and the fourth pump is configured to pump spent peritoneal dialysate from the peritoneum of the peritoneal dialysis patient into the peritoneal dialysate circuit;
the dialysate reservoir in fluid communication with the manifold;
a filter in fluid communication with the manifold;
a sorbent cartridge in fluid communication with the manifold;
a scale configured to weigh the dialysate reservoir; and
a heater configured to heat dialysate in the dialysate reservoir.

* * * * *